(12) United States Patent
Yamada et al.

(10) Patent No.: US 11,911,004 B2
(45) Date of Patent: Feb. 27, 2024

(54) BENDING AND EXTENDING DEVICE AND BENDING AND EXTENDING METHOD

(71) Applicant: NATIONAL UNIVERSITY CORPORATION SHIGA UNIVERSITY OF MEDICAL SCIENCE, Otsu (JP)

(72) Inventors: Atsushi Yamada, Otsu (JP); Tohru Tani, Otsu (JP); Shigeyuki Naka, Otsu (JP); Shigehiro Morikawa, Otsu (JP)

(73) Assignee: NATIONAL UNIVERSITY CORPORATION SHIGA UNIVERSITY OF MEDICAL SCIENCE, Shiga (JP)

( * ) Notice: Subject to any disclaimer, the term of this patent is extended or adjusted under 35 U.S.C. 154(b) by 1105 days.

(21) Appl. No.: 16/343,990

(22) PCT Filed: Oct. 24, 2017

(86) PCT No.: PCT/JP2017/038239
§ 371 (c)(1),
(2) Date: Apr. 22, 2019

(87) PCT Pub. No.: WO2018/079504
PCT Pub. Date: May 3, 2018

(65) Prior Publication Data
US 2019/0335977 A1  Nov. 7, 2019

(30) Foreign Application Priority Data
Oct. 24, 2016 (JP) ................................. 2016-208103

(51) Int. Cl.
*A61B 1/008* (2006.01)
*A61M 25/01* (2006.01)
(Continued)

(52) U.S. Cl.
CPC .............. *A61B 1/008* (2013.01); *A61B 34/70* (2016.02); *A61M 25/0133* (2013.01);
(Continued)

(58) Field of Classification Search
CPC .............. A61B 1/008; A61B 2034/301; A61M 25/0105; A61M 25/0133; A61M 25/0144; A61M 25/0147
See application file for complete search history.

(56) References Cited

U.S. PATENT DOCUMENTS 5,824,031 A * 10/1998 Cookston .......... A61M 25/0155
607/122
5,882,333 A * 3/1999 Schaer .............. A61M 25/0144
604/95.01

(Continued)

FOREIGN PATENT DOCUMENTS

JP  2005-144188 A  6/2005
JP  2009-516571 A  4/2009
(Continued)

OTHER PUBLICATIONS

Extended European Search Report dated Aug. 3, 2020 from corresponding EP Patent Application No. 17864872.1, 7 pages.
(Continued)

*Primary Examiner* — Todd J Scherbel
(74) *Attorney, Agent, or Firm* — MH2 TECHNOLOGY LAW GROUP, LLP

(57) ABSTRACT

A bending and extending device 1 comprises an elastic hollow guide unit 2 and a movable part 3 to be movably inserted into the guide unit 2. The movable part 3 is constituted, either partially or entirely, of a plurality of belt-like flexible parts 30a and 30b, which extend in the axial direction of the guide unit 2 and the flexible parts 30a and 30b are connected at distal ends. The bending and
(Continued)

extending device 1 is characterized in that, when, by the sliding operation of the flexible parts 30a and 30b, a cross-section in which a contact point T of the flexible part 30a and the inner surface of the guide unit 2 is present on an extending line Y extending from a line segment connecting the centroid P of the flexible part 30b and the axial center G of the guide unit 2 and in which the flexible part 30a and the second flexible part 30b are in contact with each other is generated, and when the cross-section is divided into two ranges by a predetermined straight line X, the centroid P of the flexible part 30b is not positioned in a range in which the contact point T is present; and the predetermined straight line X is a line that passes through the axial center G of the guide unit 2, and that orthogonally crosses the extending line Y.

11 Claims, 30 Drawing Sheets

(51) Int. Cl.
*A61B 34/00* (2016.01)
*A61B 34/30* (2016.01)
*A61M 25/09* (2006.01)
*B25J 19/00* (2006.01)

(52) U.S. Cl.
CPC ............... *A61B 2034/301* (2016.02); *A61M 2025/0915* (2013.01); *B25J 19/00* (2013.01)

(56) References Cited

U.S. PATENT DOCUMENTS

| | | | |
|---|---|---|---|
| 7,077,823 B2 * | 7/2006 | McDaniel | A61M 25/0147 604/95.01 |
| 7,449,002 B1 * | 11/2008 | Wenstad | A61M 25/09041 600/585 |
| 2005/0107737 A1 | 5/2005 | McDaniel | |

FOREIGN PATENT DOCUMENTS

| | | |
|---|---|---|
| JP | 2015-192845 A | 11/2015 |
| WO | 00/22981 A1 | 4/2000 |
| WO | 01/13812 A1 | 3/2001 |
| WO | 2007/061702 A2 | 5/2007 |

OTHER PUBLICATIONS

International Search Report dated Dec. 5, 2017 from International Application No. PCT/JP2017/038239, 4 pages, Including English translation.

* cited by examiner

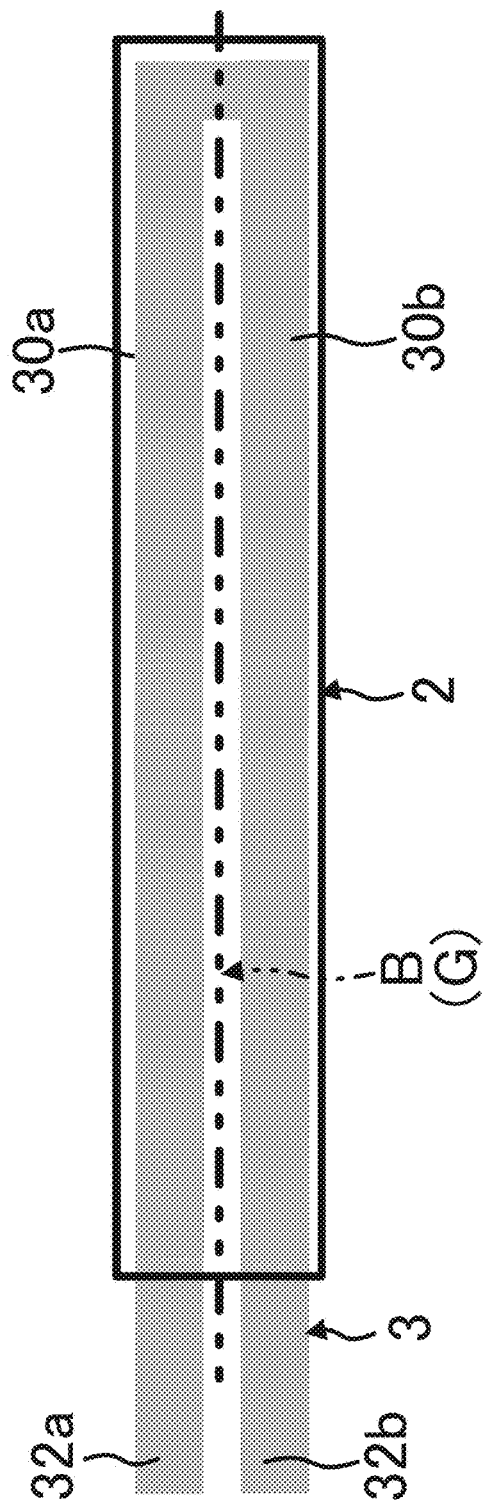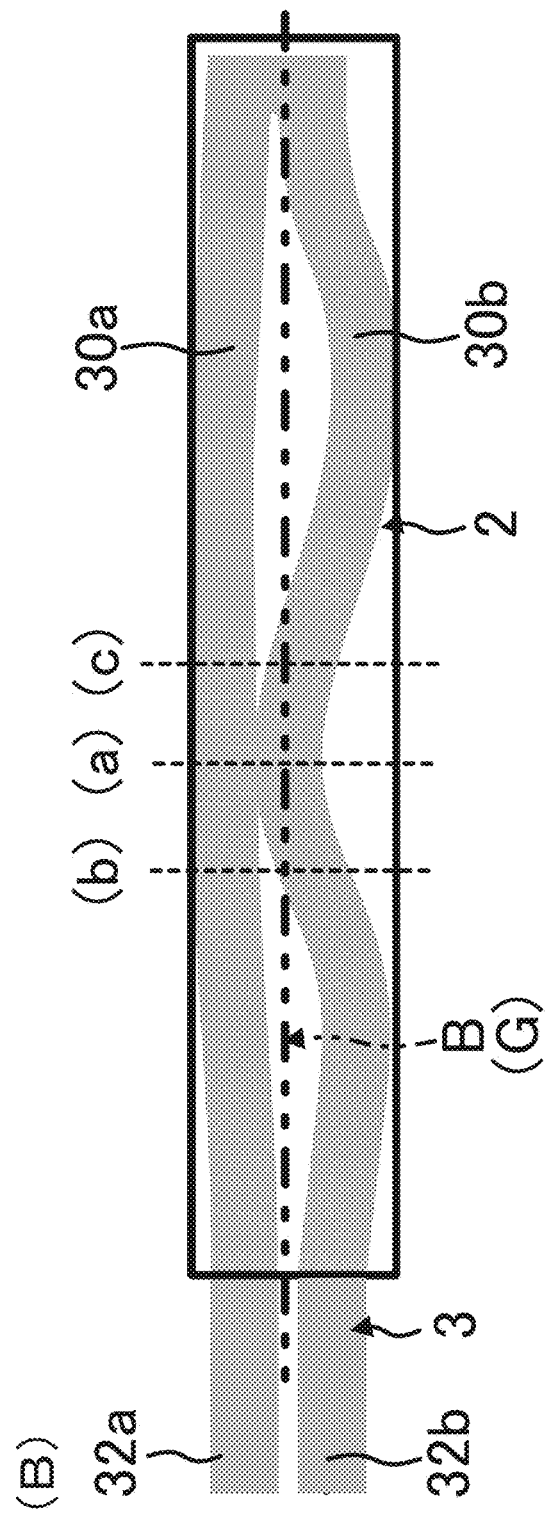
Fig.9

BENDING AND EXTENDING DEVICE AND BENDING AND EXTENDING METHOD

CROSS-REFERENCE TO RELATED APPLICATIONS

This application is a U.S. National Stage application of PCT/JP2017/038239 filed 24 Oct. 2017, which claims priority to Japanese Application No. 2016-208103 filed 24 Oct. 2016, the entire disclosures of which are incorporated herein by reference.

TECHNICAL FIELD

The present invention relates to a bending and extending device, and a bending and extending method, that makes it possible to bend and extend a hollow elastic material by utilizing a spring action in various devices such as a surgical instrument, an endoscope, an apparatus having a surgical instrument and an endoscope, a movable catheter, a movable needle, a robot arm structure, a manipulator, a biopsy needle, and the like.

BACKGROUND ART

As shown in FIG. 28, the inventors of the present invention suggested, as a bending and extending device, a device 100 comprising a guide unit 200 and a movable part 300, which are independent from each other (Patent Document 1).

The guide unit 200 is a long, hollow elastic body having an opening at each end.

The movable part 300 is constituted of two belt-like flexible parts 301a and 301b connected at their distal ends. The flexible parts 301a and 301b have a rigidity equal to or greater than that of the guide unit 200. A part or the entirety of the movable part 300 (flexible parts 301a and 301b) can be inserted into the guide unit 200 through an opening at an end of the guide unit 200.

When the bending and extending device 100 is used, first, the movable part 300 is inserted into the guide unit 200. Then, a proximal end 302, which is one of the proximal ends 302a and 302b of the two flexible parts 301a and 301b constituting the movable part 300, is made to slide relative to the other proximal end 302 in the axial direction A of the guide unit 200. As a result, bending is generated in the movable part 300 at the distal end T of the flexible parts 301a and 301b, which serves as a node, in the direction B (hereinafter referred to as relative direction B), which is the relative direction of the flexible parts 301a and 301b; and the movable part 300 thus bent comes into contact with a part or the entirety of the inner surface of the guide unit 200, thereby bending the guide unit 200 in the relative direction B.

Further, by sliding the proximal end of flexible part 301a or 301b in the direction opposite to the bending direction, the movable part 300 thus bent is extended and comes into contact with a part or the entirety of the inner surface of the guide unit 200 that is bent. As a result, the guide unit 200 is also extended.

CITATION LIST

Patent Documents

Patent Document 1: JP2015-192845A

SUMMARY OF INVENTION

Technical Problem

When the bending and extending device 100 is inserted into a body as a movable catheter, the guide unit 200 is subjected to an external force by coming into contact with a vascular wall, an organ, and the like. Further, since the guide unit 200 is constituted of a long, hollow elastic body, if the external force is large, the external force is transmitted to the movable part 300 through the guide unit 200, thereby causing buckling of the movable part 300 (FIG. 29 shows a state in which the movable part 300 is buckled by fixing the flexible part 301a, and pulling the flexible part 301b toward one side of the axial direction A). Although this buckling occurs within the elastic deformation range of the movable part 300, the buckling may cause large bending of the guide unit 200 halfway through the operation; or may cause unexpected deformation of the guide unit 200.

When the bending and extending device 100 is used as a catheter, the length of the bending and extending device 100 is set to about 1,500 mm. However, when the bending and extending device 100 is thus long, when the guide unit 200 or the movable part 300 is bent by the operation of sliding the flexible part 301a, 301b in the axial direction A, the distance D between the flexible parts 301a and 301b becomes large, as shown in FIG. 30. As a result, it is possible that the flexible parts 301a and 301b may be twisted; or may intersect with each other, thereby failing to deform the bending and extending device 100 to a desired shape.

The present invention was made in light of the matters described above, and an object of the present invention is to provide a bending and extending device having an advantageous structure in terms of preventing unexpected local bending due to buckling, as well as a method for bending and extending the bending and extending device.

Solution to Problem

In order to achieve the object, the present invention encompasses the inventions in the following items.

Item 1. A bending and extending device, comprising:
an elastic hollow guide unit; and
a movable part to be movably inserted into the guide unit, wherein:
the movable part is constituted, either partially or entirely, of a plurality of belt-like flexible parts, which extend in the axial direction of the guide unit and are connected at distal ends; the movable part causes the plurality of flexible parts to be bent in the direction perpendicular to the axial direction of the guide unit by sliding one of proximal ends of the plurality of flexible parts in the axial direction of the guide unit (hereinafter referred to as a flexible part sliding operation);
when, by the sliding operation, a cross-section in which a contact point of a second flexible part and the inner surface of the guide unit is present on an extending line extending from a line segment connecting the centroid of a first flexible part and the axial center of the guide unit, and in which the first flexible part and the second flexible part are directly or indirectly in contact with each other is generated, and when the cross-section is divided into two ranges by a predetermined straight line, the centroid of the first flexible part is not positioned in a range in which the contact point of the second flexible part and the inner surface of the guide unit is present; and the predetermined straight line is a line that passes through the axial center of the guide unit, and that orthogonally crosses the extending line.

Item 2. The bending and extending device according to item 1, wherein the movable part is constituted, either partially or entirely, of three or more flexible parts.

Item 3. The bending and extending device according to item 1, wherein each flexible part has a range (hereinafter referred to as a divided range) having a cross-sectional shape corresponding to one of the planes obtained by equally dividing the internal cross-section of the guide unit by the number of the flexible parts; and, in a state in which the movable part is inserted into the guide unit so that the divided range of each flexible part is positioned in the guide unit, a combination of the cross-sections of the divided ranges of each flexible part substantially coincides with the internal cross-section of the guide unit; and a side surface of the divided range of the first flexible part and a side surface of the divided range of another flexible part opposite thereto are parallel to each other.

Item 4. The bending and extending device according to item 3, wherein the internal cross-section of the guide unit has a circular shape; the movable part is constituted, either partially or entirely, of two flexible parts; and the cross-sectional shape of the divided range of each flexible part corresponds to one of semicircular planes obtained by equally dividing the internal cross-section of the guide unit into two planes.

Item 5. The bending and extending device according to item 3, wherein the internal cross-section of the guide unit has a rectangular shape; the movable part is constituted, either partially or entirely, of two flexible parts; and the cross-sectional shape of the divided range of each flexible part corresponds to one of rectangular planes obtained by equally dividing the internal cross-section of the guide unit into two planes.

Item 6. The bending and extending device according to item 3, wherein the internal cross-section of the guide unit has a circular shape; the movable part is constituted, either partially or entirely, of four flexible parts; and the cross-sectional shape of the divided range of each flexible part corresponds to one of fan-shaped planes obtained by equally dividing the internal cross-section of the guide unit into four planes.

Item 7. The bending and extending device according to any one of items 1 to 6, wherein each flexible part has a thin portion at a distal end side or a proximal end side.

Item 8. The bending and extending device according to any one of items 1 to 7, wherein the plurality of flexible parts have elasticity greater than that of the guide unit.

Item 9. The bending and extending device according to item 8, wherein the guide unit is formed of a hyperelastic alloy such as β titanium, nickel titanium (nitinol), or stainless steel, a resin material, or rubber; and the plurality of flexible parts are formed to have a rigidity equal to or greater than that of the guide unit using β titanium, nickel titanium, polypropylene, an acrylic material, or PEEK (polyether ether ketone) resin.

Item 10. The bending and extending device according to any one of items 1 to 9, wherein the movable part is rotatable in the circumferential direction of the guide unit.

Item 11. A method for bending and extending the bending and extending device according to any one of items 1 to 10, comprising:
an insertion step of inserting the movable part into the guide unit so that the movable part extends in the axial direction of the guide unit;
a sliding step of sliding a proximal end of a first flexible part, which is one of the plurality of flexible parts, relative to a proximal end of another flexible part in the axial direction of the guide unit;
an inverse sliding step of sliding the proximal end of the first flexible part in the direction opposite to the direction upon the bending;
wherein:
by the sliding step, bending is generated in the movable part at the distal end of the flexible part serving as a node in a direction perpendicular to the axial direction of the guide unit, and the movable part thus bent comes into contact with a part or the entirety of the inner surface of the guide unit, thereby causing the guide unit to be bent in the perpendicular direction; and by the inverse sliding step, the movable part thus bent is extended and comes into contact with a part or the entirety of the inner surface of the guide unit, thereby extending the guide unit.

Item 12. The bending and extending method according to item 11, further comprising a rotation step of rotating the movable part inserted in the guide unit in the circumferential direction of the guide unit, thereby changing the direction of the movable part, wherein the change in the direction of the movable part by the rotation step changes the direction of the bending generated in the guide unit in the sliding step.

BRIEF DESCRIPTION OF DRAWINGS

FIG. 9: (A) is a lateral view before the sliding operation of a flexible part, and (B) is a lateral view after the sliding operation of a flexible part.

DESCRIPTION OF EMBODIMENTS

The bending and extending device, and the bending and extending method, of the present invention may be used to cause bending and extending of a hollow guide unit in various devices such as a surgical instrument, an endoscope, an apparatus having a surgical instrument and an endoscope, a movable catheter, a movable needle, a robot arm structure, a manipulator, a biopsy needle, and the like. An embodiment of the present invention is explained below with reference to the drawings. In the following embodiment, the bending and extending device of the present invention is used as a catheter; however, the bending and extending device of the present invention can be applied to various devices, and the application thereof is not limited to catheters.

Figure 1:
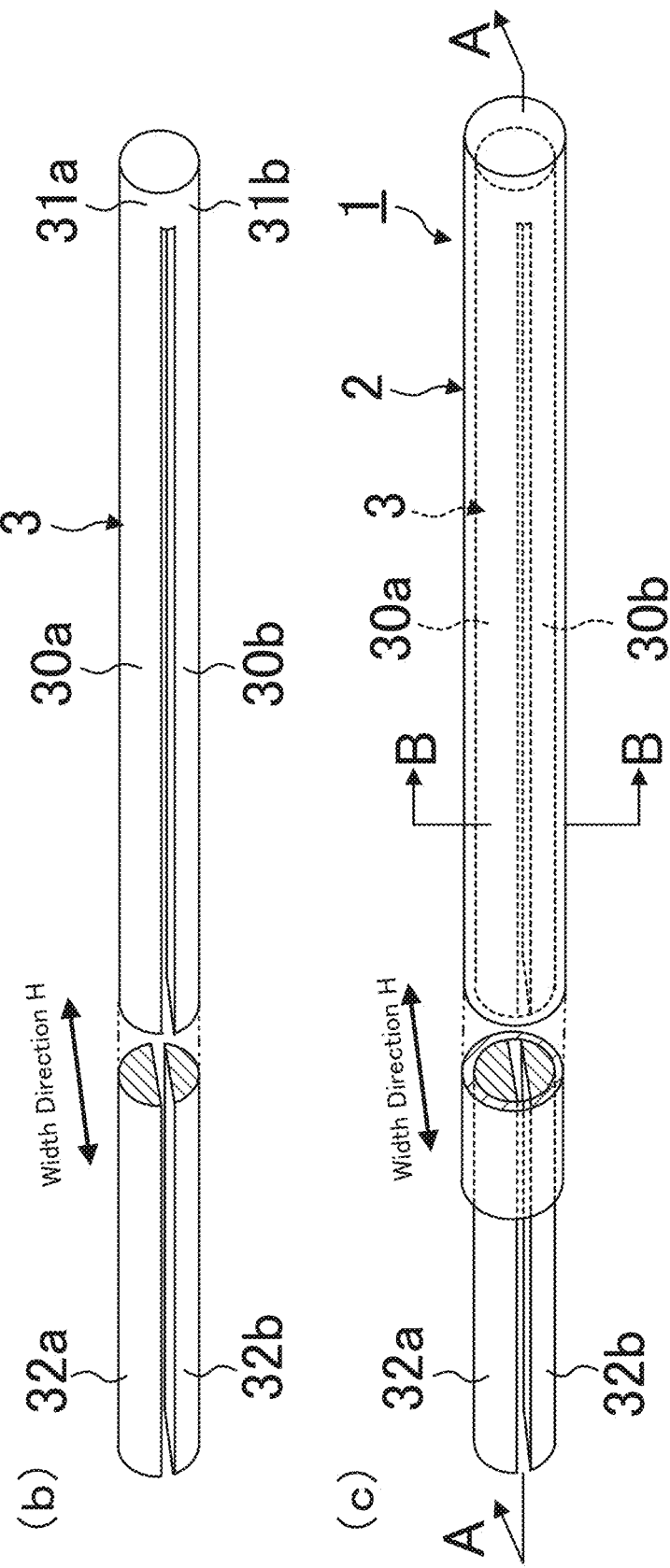
FIG. 1: (a) is a perspective view showing a guide unit, (b) is a perspective view showing a movable part, and (c) is a perspective view showing a bending and extending device according to an embodiment of the present invention.
Figure 2:
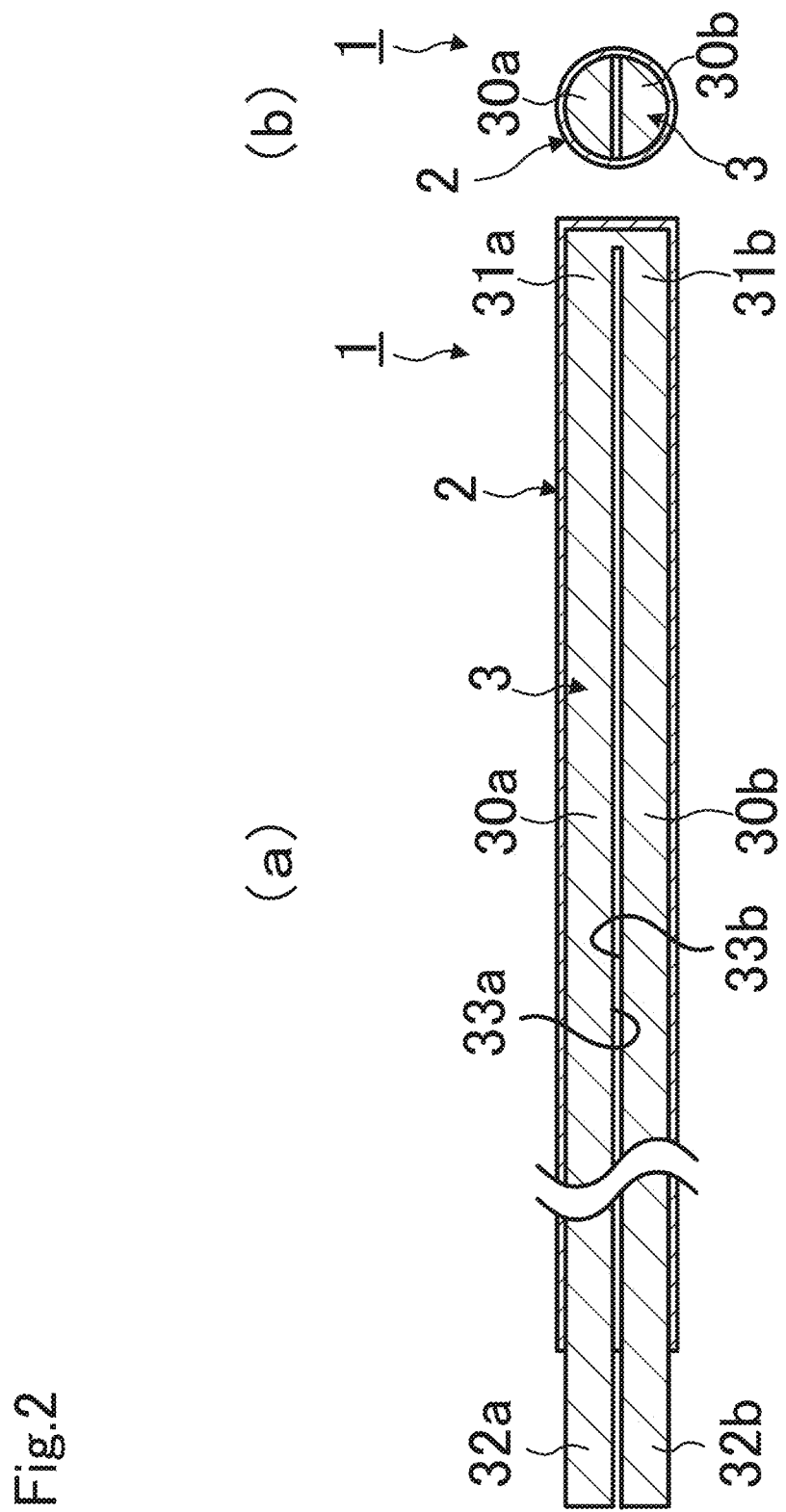
FIG. 2: (a) is a cross-sectional view, taken along line A-A in FIG. 1 (c); and (b) is a cross-sectional view, taken along line B-B in FIG. 1 (c).
Figure 3:
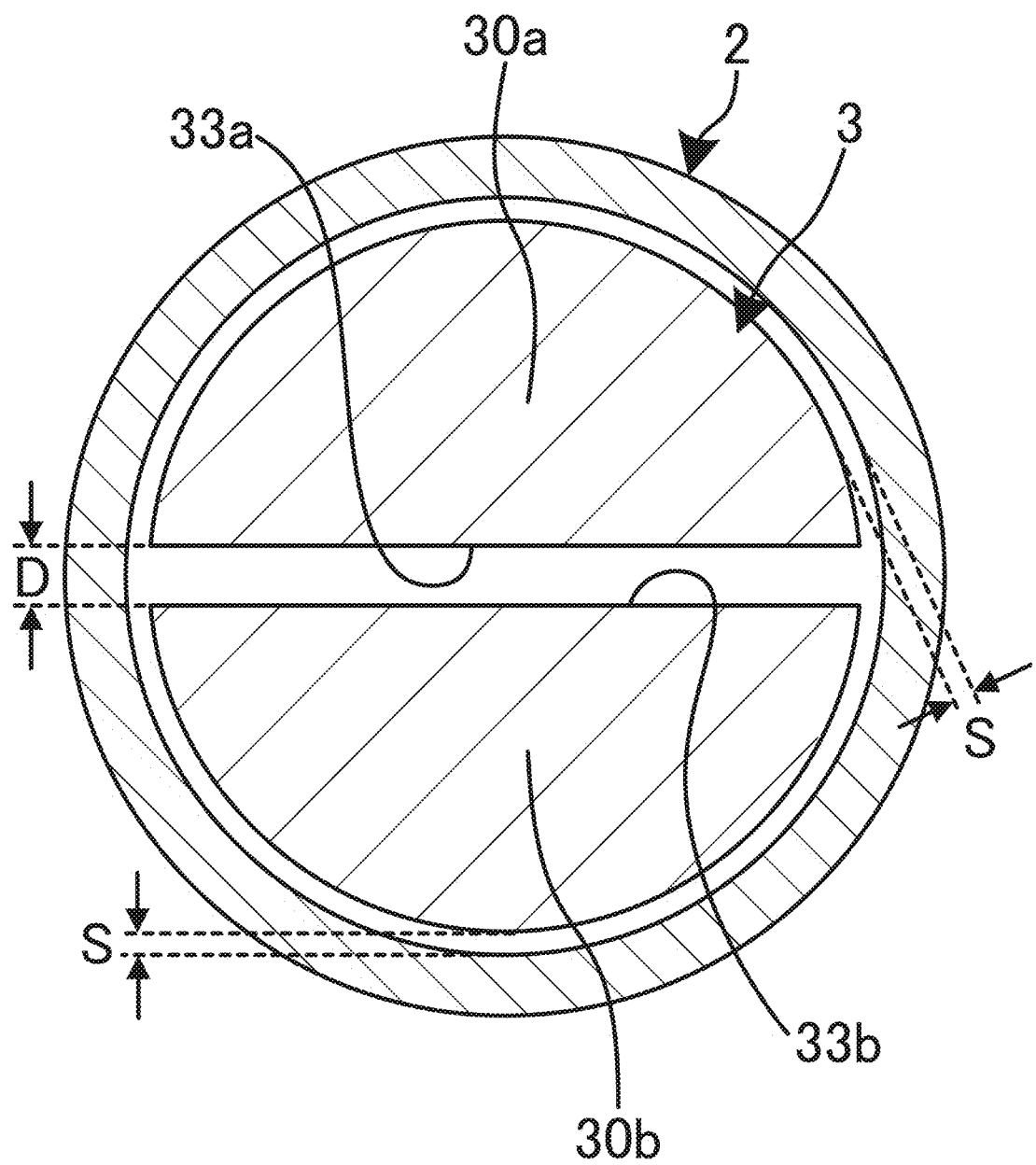
FIG. 3 is a magnified view of FIG. 2 (b).
Figure 4:
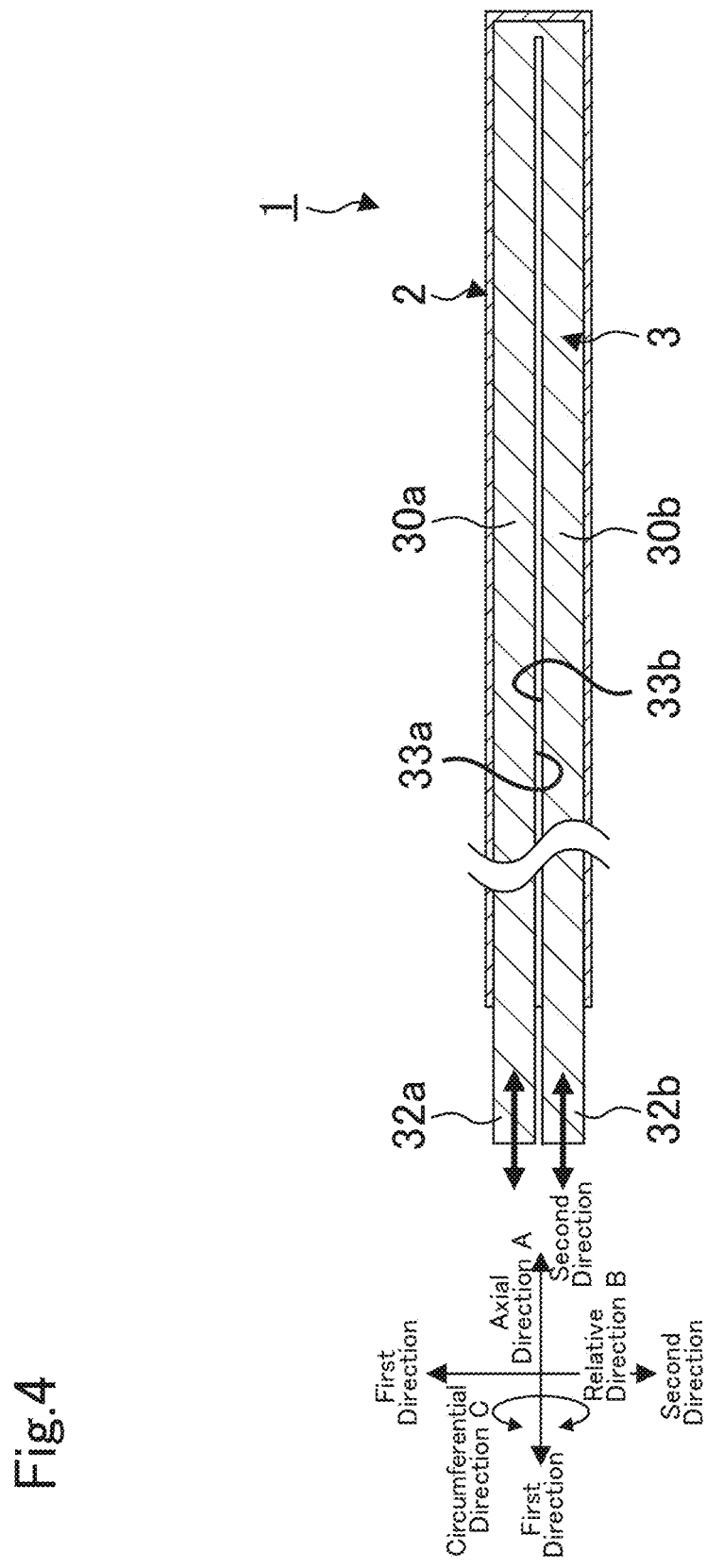
FIG. 4 is a cross-sectional view corresponding to FIG. 2 (a), showing the sliding direction of the movable part 3.

FIG. 1 is a perspective view showing a part and the entire bending and extending device 1 according to an embodiment of the present invention. FIG. 1 (a) shows a guide unit 2 described later, FIG. 1 (b) shows a movable part 3 described later, FIG. 1 (c) shows a bending and extending device 1, FIG. 2 (a) is a cross-sectional view, taken along line A-A in FIG. 1 (c), and FIG. 2 (b) is a cross-sectional view, taken along line B-B in FIG. 1 (c). FIG. 3 is a magnified view of FIG. 2 (b). FIG. 4 is a cross-sectional view corresponding to FIG. 2 (a), showing the sliding direction of the movable part 3 described later. In FIG. 1, FIG. 2, and FIG. 4, some parts of the guide unit 2, the movable part 3, and the bending and extending device 1 are omitted.

As shown in FIGS. 1 to 4, the bending and extending device 1 comprises, as functional modules, a hollow guide unit 2 that is elastic and deformable, and a movable part 3 that is movably inserted into the guide unit 2. This bending and extending device 1 is used as a catheter to be inserted into a body, and the lengths of the guide unit 2 and the movable part 3 are set to about 1,500 The lengths of the guide unit 2 and the movable part 3 are not limited to this length, and may be changed as appropriate.

The guide unit 2 is preferably formed of an elastic material having a small residual stress. Examples of the material of the guide unit 2 include hyperelastic alloys, such as β titanium, nickel titanium (nitinol), or stainless steel, resin materials, rubber, and the like.

An instrument (not shown) such as a camera may be provided inside or at the distal end of the guide unit 2. A wiring (not shown) for supplying electricity to the instrument may be provided along the inner surface of the guide unit 2. Further, in addition to the movable part 3, a therapeutic needle or a hollow tube may also be inserted into the guide unit 2.

The movable part 3 is constituted, either partially or entirely, of two belt-like flexible parts 30a and 30b that extend in the axial direction of the guide unit 2 (FIGS. 1 to 4 show an example in which the entire movable part 3 is constituted of the flexible parts 30a and 30b).

The flexible parts 30a and 30b are elastic bands each having a predetermined width, and are constituted as a plate-shaped spring. The flexible parts 30a and 30b are connected through their ends 31a and 31b. More specifically, the movable part 3 has a structure in which long elastic bands are connected at the distal end, or folded at the distal end. In the movable part 3, the two flexible parts 30a and 30b are in relative positions.

The flexible parts 30a and 30b are formed to have a rigidity equal to or greater than that of the guide unit 2 using β titanium, nickel titanium, polypropylene, an acrylic material, or PEEK (polyether ether ketone) resin. When the guide unit 2 has a significantly small thickness, and the flexible parts 30a and 30b are thicker than the guide unit 2, the flexible parts 30a and 30b are preferably formed of β titanium or nickel titanium.

Further, the flexible parts 30a and 30b have a form such that the cross-section thereof corresponds to one of the planes obtained by equally dividing the internal cross-section of the guide unit 20 by the number of flexible parts 30. More specifically, the internal cross-section of the guide unit 2 has a circular shape, and the cross-sectional shape of each flexible part 30a and 30b corresponds to a semicircular plane obtained by equally dividing the internal cross-section of the guide unit 2 into two planes. The above structure in which the shape of the cross-section corresponds to one of the divided planes (semicircular planes) means one of the following (1) to (3).

(1) The "shape of the cross-section" described above coincides with "the shape of the divided plane (semicircular plane)" described above.
(2) The "shape of the cross-section" described above coincides with "the shape resulting from similarity reduction of the divided plane (semicircular plane)" described above.
(3) The "shape of the cross-section" described above coincides with "the shape resulting from reduction in width or thickness of the divided plane (semicircular plane)" described above.

As shown in FIG. 1 (c) and FIGS. 2 to 4, in a state in which the movable part 3 is inserted into the guide unit 2 so that the flexible parts 30a and 30b are positioned inside the guide unit 2, the shape of the combination of the cross-sections of the flexible parts 30a and 30b substantially coincides with the circular shape of the internal cross-section of the guide unit 2 (FIG. 2 (b), FIG. 3). Further, the side surface 33a of the flexible part 30a and the side surface 33b of the flexible part 30b opposite to the side surface 33a both form a plane extending in the axial direction A of the guide unit 2 (FIG. 4), and become parallel to each other.

Further, the proximal ends 32a and 32b of the flexible parts 30a and 30b are extended to the outside of the guide unit 2. When the bending and extending device 1 is used as a catheter, an operation unit (not shown) is connected to the proximal ends 32a and 32b of the flexible parts 30a and 30b. By operating the operation unit, the following operations (1) and (2) can be carried out.

(1) One (proximal end 32) of the proximal ends 32a and 32b of the flexible parts 30a and 30b is made to slide relative to the other proximal end 32 in the axial direction A of the guide unit 2 (FIG. 4).
(2) The entire movable part 3 is moved in the axial direction A of the guide unit 2 (FIG. 4).

Figure 5:
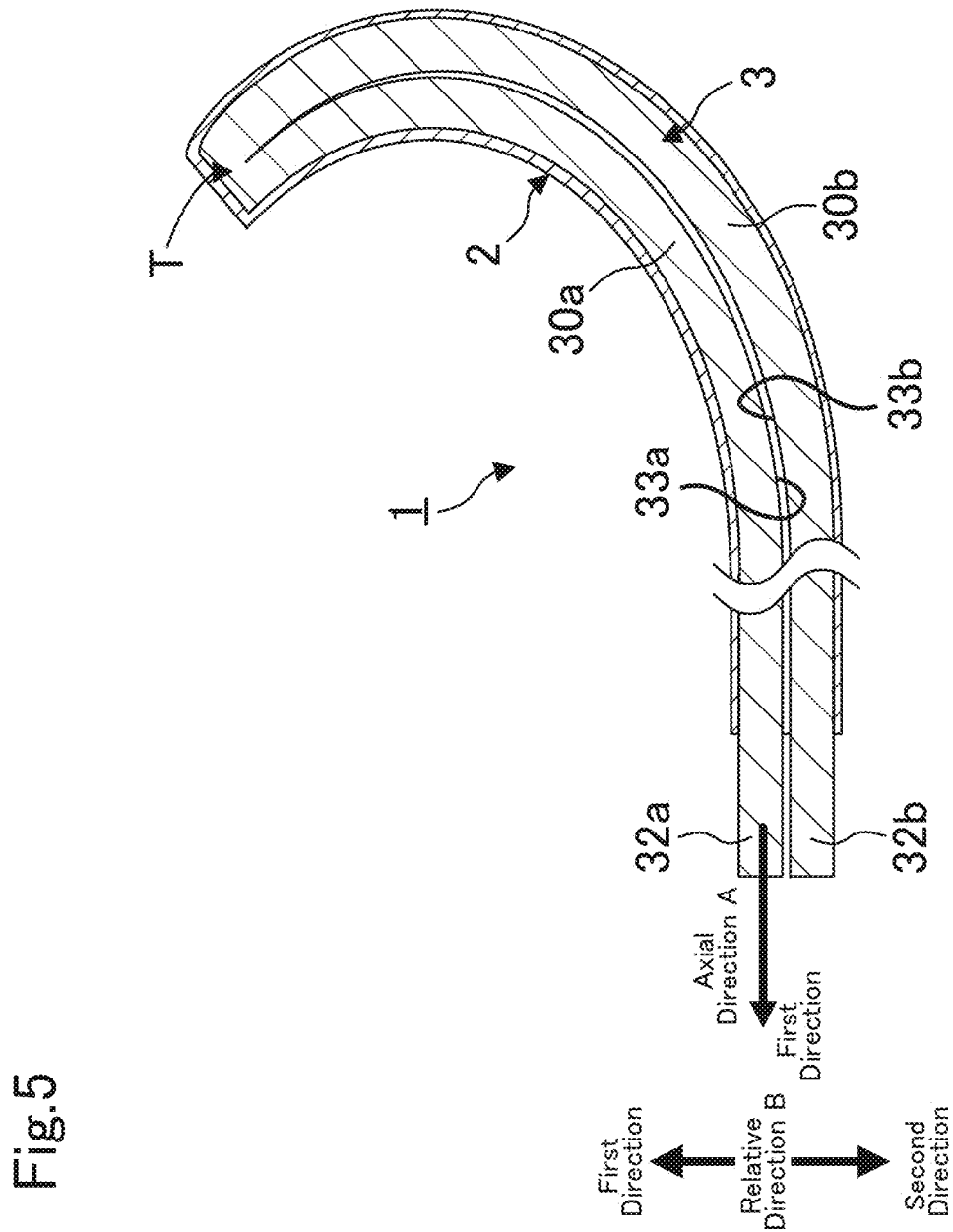
FIG. 5 is a schematic cross-sectional view showing a state in which a bending and extending device is bent.

FIG. 5 is a schematic cross-sectional view showing a state in which the bending and extending device 1 is bent by the sliding operation described in (1) above.

As in (1) above, when the proximal ends 32a and 32b of the flexible parts 30a and 30b are made to relatively slide, as shown in FIG. 5, the movable part 3 is bent at the distal end T of the flexible parts 30a and 30b, which serves as a node, in the direction B (hereinafter referred to as relative direction B) in which the flexible parts 30a and 30b are opposed; and the movable part 3 thus bent comes into contact with a part or the entirety of the inner surface of the guide unit 2. As a result, bending in the relative direction B is also generated in the guide unit 2. The bending of the guide unit 2 means that the entirety or a part of the guide unit 2 is bent in an arciform manner or the like, or that the guide unit 2 is expanded (expanded in diameter). For example, when the guide unit 2 is made of a shrinkable rubber material having high elasticity, as the movable part 3 with high rigidity comes into contact with the guide unit 2, the guide unit 2 is expanded along the deformation of the movable part 3 (expanded in diameter). When the guide unit 2 is made of an unshrinkable material, as the movable part 3 with high rigidity comes into contact with the guide unit 2, the entirety or a part of the guide unit 2 is bent in an arciform manner.

The example shown in FIG. 5 shows a case in which the proximal end 32a of the flexible part 30a is made to slide in one side of the axial direction A with the proximal end 32b of the flexible part 30b stopped at a fixed position. As a result, bending occurs in one side of the relative direction B in the flexible parts 30a and 30b, and the guide unit 2.

In contrast to the example of FIG. 5, the proximal end 32b of the flexible part 30b may be made to slide in one side of the axial direction A with the proximal end 32a of the flexible part 30a stopped at a fixed position. In this case, bending in the other side of the relative direction B is generated in the flexible parts 30a and 30b, and the guide unit 2 (bending occurs in a direction opposite to that in the example of FIG. 5).

Further, among the proximal ends 32a and 32b of the flexible parts 30a and 30b, one proximal end 32 may be made to slide in the other direction (second direction) of the axial direction A (see FIG. 4). For example, in the case in which the proximal end 32a of the flexible part 30a is made to slide in the other side (second direction) of the axial direction A with the proximal end 32b of the flexible part 30b stopped at a fixed position, bending in the other side of the relative direction B is generated in the flexible parts 30a and 30b, and the guide unit 2 (bending occurs in a direction opposite to that in the example of FIG. 5).

Further, after the movable part 3 and the guide unit 2 are bent as described above, the movable part 3 and the guide unit 2 can be extended by sliding the proximal ends 32a and 32b of the flexible parts 30a and 30b in the direction opposite to the direction upon bending. More specifically, by sliding it in the reverse direction, the movable part 3 thus bent is extended and comes into contact with a part or the entirety of the inner surface of the guide unit 2 that is bent; as a result, the guide unit 2 is extended.

For example, as shown in FIG. 5, in the case of bending the movable part 3 and the guide unit 2 by sliding the proximal end 32a of the flexible part 30a in one side (first direction) of the axial direction A, the movable part 3 and the guide unit 2 can be extended by sliding the proximal end 32a of the flexible part 30a in the other direction (second direction) of the axial direction A, which is opposite to the direction upon bending. To generate the above bending and extension, both the proximal ends 32a and 32b of the flexible parts 30a and 30b may be made to slide in different lengths. In this manner, it is possible to change the size of bending (bending deformation) and extension generated in the movable part 3 and the guide unit 2.

With the operation of sliding the movable part 3 in the axial direction A of the guide unit 2 shown in (2) above, it is possible to change the starting point of the bending and extension of the guide unit 2. For example, in a state in which the distal end T of the flexible parts 30a and 30b is positioned in the vicinity of the distal end of the guide unit 2, the guide unit 2 is bent at a node in the vicinity of the distal end. For example, in the case of shifting the distal end T of the flexible parts 30a and 30b to be distant from the distal end of the guide unit 2 by moving the movable part 3, the distal end portion of the guide unit 2 is not bent.

Further, when the movable part 3 and the guide unit 2 are independent from each other, the movable part 3 has a large thickness and a length as short as a common needle, and the movable part 3 has high rigidity, it is possible to rotate the movable part 3 of the guide unit 2 in the circumferential direction C. With this rotation operation, it is possible to change the direction of the movable part 3; therefore, it is possible to change the bending direction of the guide unit 2. The relationship between the direction of the movable part 3 and the bending direction of the guide unit 2 is specifically explained below with reference to FIGS. 6 and 7.

Figure 6:
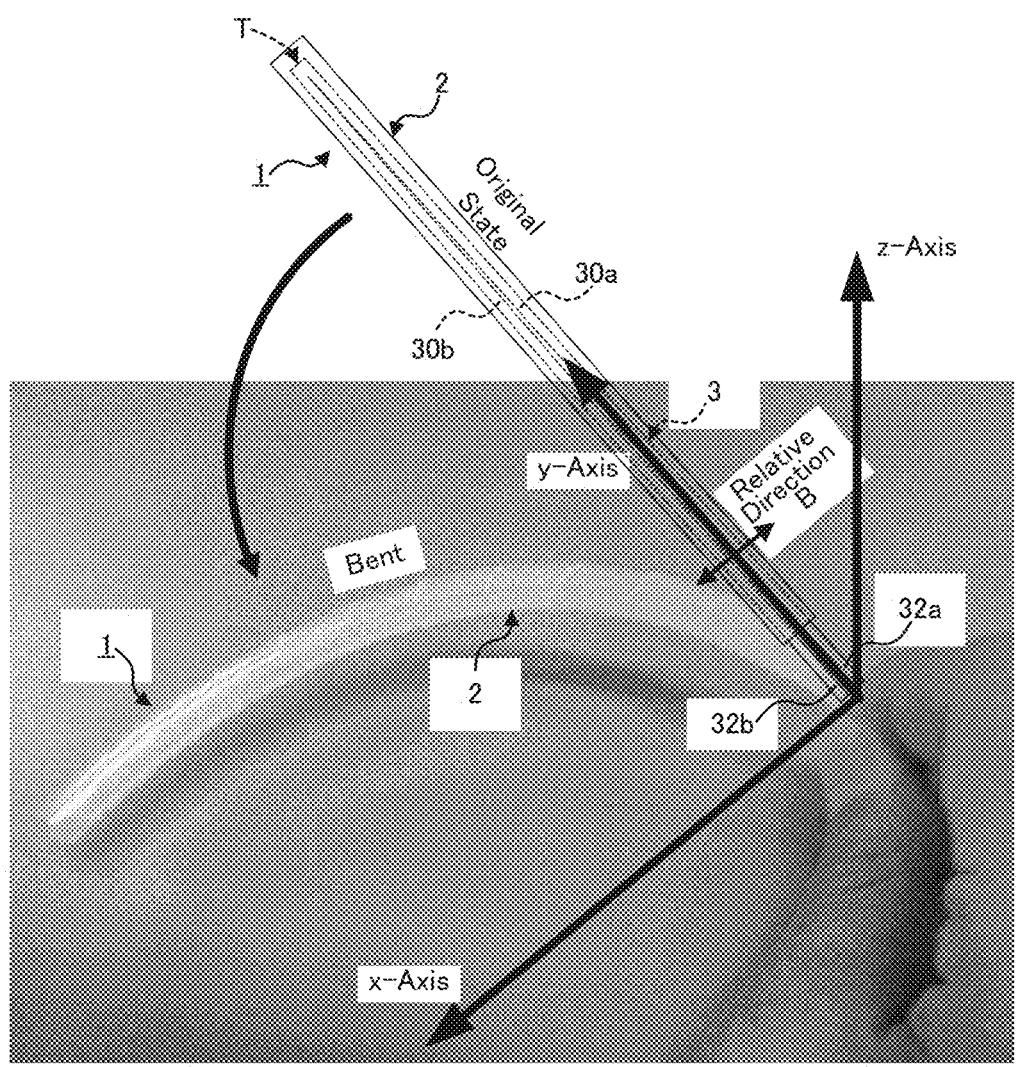
FIG. 6 is a figure showing the bending direction of a guide unit when the relative direction of a flexible part is oriented to the x-axis direction.

FIG. 6 shows the bending direction of the guide unit 2 when the relative direction B of the flexible parts 30a and 30b is the x-axis direction (see FIGS. 4 and 5 regarding the relative direction B). At first, the axial directions of the guide unit 2 and the movable part 3 extend in the y-axis direction. By relatively sliding the proximal ends 32a and 32b of the flexible parts 30a and 30b in the y-axis direction from this original state, the movable part 3 is bent in the horizontal plane (XY plane) along the relative direction B. Further, as the movable part 3 thus bent comes into contact with the inner surface of the guide unit 2, the guide unit 2 is bent in the horizontal plane (XY plane).

Figure 7:
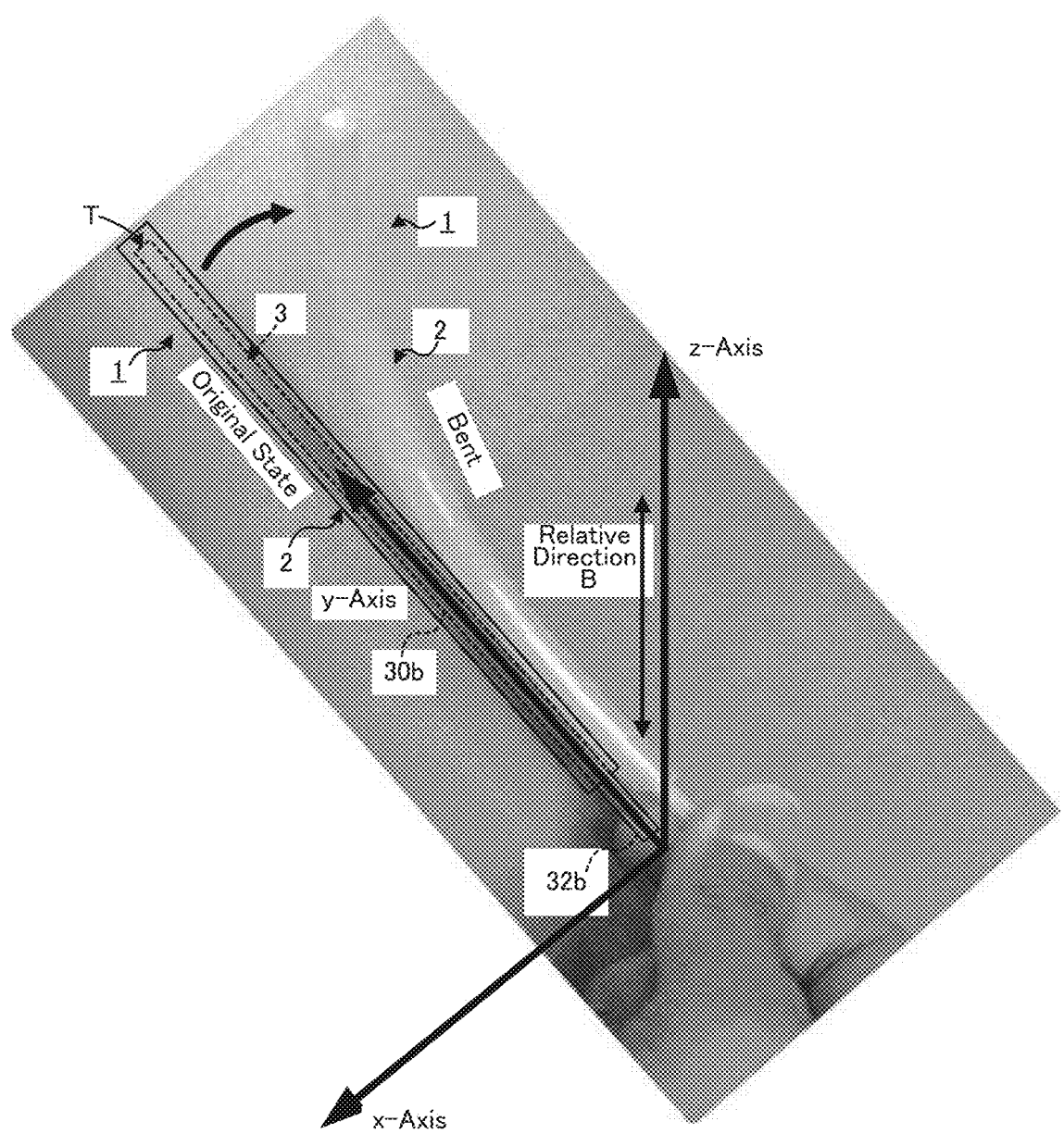
FIG. 7 is a figure showing the bending direction of a guide unit when the relative direction of a flexible part is oriented to the Z-axis direction by rotating a movable part about 90 degrees in the circumferential direction of the guide unit 2 from the state shown in FIG. 6.

FIG. 7 is a figure showing the bending direction of the guide unit 2 when the relative direction B of the flexible parts 30a and 30b is oriented to the Z-axis direction by rotating the movable part 3 about 90 degrees in the circumferential direction C (FIG. 4) of the guide unit 2 from the state shown in FIG. 6. At first, the axial directions of the guide unit 2 and the movable part 3 extend in the y-axis direction. By relatively sliding the proximal ends 32a and 32b of the flexible parts 30a and 30b in the y-axis direction from this original state, the movable part 3 is bent in the vertical plane (YZ plane) along the relative direction B. Further, as the movable part 3 thus bent comes into contact with the inner surface of the guide unit 2, the guide unit 2 is also bent in the vertical plane (YZ plane).

As is clear from the above, the bending of the movable part 3 and guide unit 2 is generated in the plane along the relative direction B. Therefore, by changing the direction of the movable part 3 by the rotation operation of the movable part 3, it is possible to change the bending direction of the guide unit 2 (the plane in which the bending of the guide unit 2 is generated). Further, since the guide unit 2 can thus be bent in any direction, when a camera is provided at the distal end of the guide unit 2, the direction of the camera can be changed without rotating the camera itself.

Figure 8:
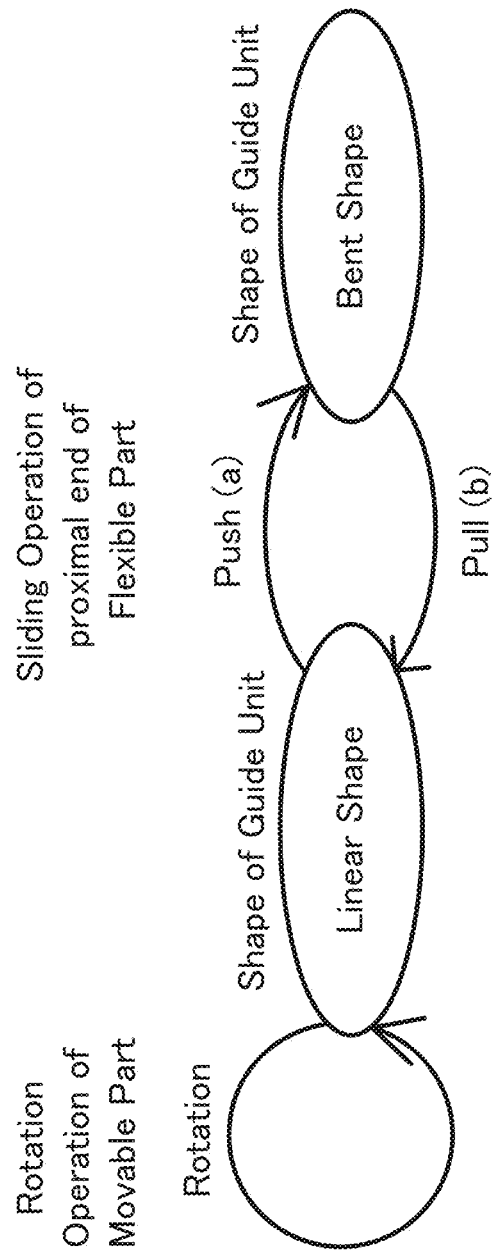
FIG. 8 is a schematic diagram showing the timing of the operation of rotating a movable part, or the operation of sliding the proximal end of a flexible part.

FIG. 8 is a schematic diagram showing the timing of the operation of rotating the movable part 3, or the operation of sliding the proximal ends 32a and 32b of the flexible parts 30a and 30b. The operation of rotating the movable part 3 is carried out when the guide unit 2 has a linear shape. Further, after the direction of the movable part 3 is changed by this rotation operation, the proximal ends 32a and 32b of the flexible parts 30a and 30b are made to slide by pushing and pulling them. As a result, the movable part 3 and guide unit 2 are bent (FIG. 8 shows an example in which the movable part 3 and the guide unit 2 are bent by pushing the proximal end 32 of the flexible part 30 (a)).

Then, after the bending, if there is a desire for the guide unit 2 to bend again in a different direction, first, the proximal ends 32a and 32b of the flexible parts 30a and 30b are made to slide by pulling or pushing them back. As a result, the movable part 3 and the guide unit 2 are extended, and the guide unit 2 returns to the linear shape (FIG. 8 shows an example in which the guide unit 2 returns to the linear shape by extending the movable part 3 by pulling back the proximal end 32 of the flexible part 30 (b)). Then, after the direction of the movable part 3 is changed by an operation of rotating the movable part 3, the proximal ends 32a and 32b of the flexible parts 30a and 30b are made to slide by pushing and pulling them. As a result, the movable part 3 and the guide unit 2 are bent in a direction different from the previous direction.

It is also possible to change the bending direction of the guide unit 2 by rotating the movable part 3 inside the guide unit 2 in the circumferential direction C (FIG. 4) while maintaining the guide unit 2 bent in a given direction. In this operation, the guide unit 2 is rotated by the rotation of the movable part 3 while keeping its bending form; as a result, the bending direction of the guide unit 2 is changed.

In the bending and extending device 1 described above, buckling may be generated in the flexible part 30 at a portion in the longitudinal direction when large bending is generated by the operation (operation of (1) above) of sliding the proximal ends 32a and 32b of the flexible parts 30a and 30b, or when an external force is exerted during the bending. However, the bending and extending device 1 of the present embodiment has an advantageous structure in terms of preventing unexpected local bending due to the buckling. The circumstances under which such bending easily occurs, and the structure for preventing the bending of the bending and extending device 1, are described below.

FIG. 9 is a schematic diagram showing results of simulation according to the finite element method when large bending is generated in the flexible part 30b by fixing the proximal end 32a of the flexible part 30a, and applying a pulling force to the proximal end 32b of the flexible part 30b (by largely sliding the proximal end 32b of the flexible part 30b in one side of the axial direction A). FIG. 9 (A) shows an initial state before the pulling force is applied, and FIG. 9 (B) shows a state when a flexible part 30 is buckled after a pulling force is applied.

In the bending and extending device 1 of the present embodiment, a phenomenon such that the flexible parts 30a and 30b are pressed in one side of the inside of the guide unit 2 occurs at the portion where buckling is generated. The example shown in FIG. 9 shows a state in which the flexible parts 30a and 30b are deformed from the state of FIG. 9 (A) to the state of FIG. 9 (B) by applying a pulling force to the proximal end 32b of the flexible part 30b. In the state shown in FIG. 9 (B), buckling is generated at the position (a), and the flexible parts 30a and 30b are pressed to one side (upper side) of the inside of the guide unit 2. In order to clearly express the relative positions of the positions of the flexible parts 30a and 30b in the longitudinal direction and the backbone curve B described later, FIG. 9 shows a state before and after a pulling force is applied to the proximal end 32b of the flexible part 30b while applying a force to the guide unit 2 so that the guide unit 2 extends straight. In FIG. 9, the guide unit 2 is not bent as in FIGS. 5 to 7 merely because a force is applied to the guide unit 2 as described above; more specifically, FIG. 9 is not intended to show a state in which the bending of the guide unit 2 does not occur upon the sliding operation of the flexible part 30 (if the force is not applied to the guide unit 2, the movable part 3 is bent and comes into contact with the inner surface of the guide unit 2 upon the sliding operation of the flexible part 30, as in the state shown in FIGS. 5 to 7; as a result, the guide unit 2 is also bent).

Figure 10:
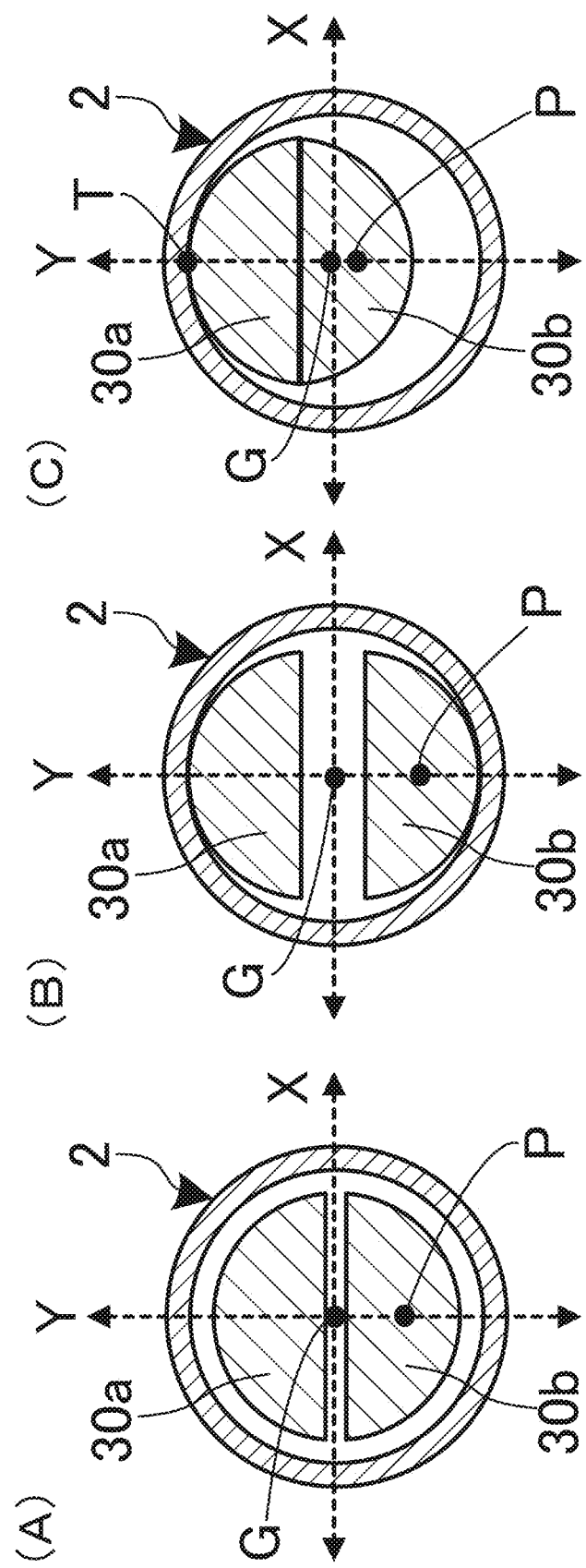
FIG. 10: (A) is a cross-sectional view showing an initial state when no pulling force is applied, (B) is a cross-sectional view showing a state when a flexible part is bent by applying a pulling force, and (C) is a cross-sectional view showing a state in which a flexible part is buckled.

FIG. 10 shows a cross-section of the bending and extending device 1 at the position (a) of FIG. 9 (B). FIG. 10 (A) shows an initial state before the pulling force is applied. FIG. 10 (B) shows a state in which the flexible parts 30a and 30b are bent by applying a pulling force. FIG. 10 (B) shows a state in which the flexible parts 30a and 30b are buckled.

In the initial state shown in FIG. 10 (A), no force is applied to the proximal ends 32a and 32b of the flexible parts 30a and 30b. In this initial state, by applying a pulling force to the proximal end 32b of the flexible part 30b while fixing the proximal end 32a of the flexible part 30a, as shown in FIG. 10 (B), the bending and extending device 1 is bent with the flexible parts 30a and 30b being lightly pressed to both sides of the guide unit 2. Further, when buckling is generated, the large deformation is generated in the flexible parts 30*a* and 30*b*, and the flexible parts 30*a* and 30*b* are pressed to one side of the guide unit 2, as shown in FIG. 10 (C).

When the shape of the cross-section of the bending and extending device 1 (i.e., the positions of the flexible parts 30*a* and 30*b* in the guide unit 2) is changed from FIG. 10 (A)→4 FIG. 10 (B)→FIG. 10 (C), the position of the cross-section (the position (a) of FIG. 9 (B)) and the rigidity of the bending and extending device 1 in the vicinity thereof change, and this rigidity change influences the bending form of the bending and extending device 1. The bending form of the bending and extending device 1 as a long and narrow elastic body can be generally expressed by the backbone curve B (FIG. 9 (B)) along the axial center G of the guide unit 2. Further, the rigidity of the bending and extending device 1 can be modeled by an elastic coefficient K=EI at each point on the backbone curve B. E is the Young's modulus determined by the material, and I is the geometrical moment of inertia determined by the shape of the cross-section.

Further, when the shape of the cross-section (i.e., the positions of the flexible parts 30*a* and 30*b* in the guide unit 2) of the bending and extending device 1 changes, the geometrical moment of inertia I'x and I'y of the flexible parts 30*a* and 30*b* based on the backbone curve B as the reference axis change. The geometrical moment of inertia I'x and I'y can be determined by formula 1 below according to the parallel axis theorem.

$$I'_x = I_x + Ay_1^2, \ I'_y = I_y + Ax_1^2$$

The formula 1 above is used to calculate the geometrical moment of inertia I'x and I'y based on the backbone curve B as the reference axis, by using the geometrical moment of inertia Ix and Iy based on the centroid. More specifically, in formula 1, Ix and Iy represent the geometrical moment of inertia about the x-axis and Y axis passing through the centroid P of the flexible part 30; A represents the cross-sectional area of the flexible part 30; and $X_1$ and $Y_1$ represent the distance from the axial center G to the centroid P of the flexible part 30 in the x-axis and y-axis directions. According to formula 1 above, if the centroid P of the flexible part 30 coincides with the axial center G, the second part on the right-hand side of each formula is 0, and the geometrical moment of inertia I'x and I'y of the flexible part 30 based on the backbone curve B as the reference axis takes the minimum values.

When buckling is generated at the position (a) in FIG. 9 (B), and the cross-section at position (A) is therefore changed from FIG. 10 (B) to FIG. 10 (C), the centroid P of the flexible part 30*b* to which a pulling force is applied is positioned lower than the x-axis in the state shown in FIG. 10 (B); therefore, the y-coordinate of the centroid P of the flexible part 30*b* takes a negative value.

Further, when the buckling is generated at the position (a), if the centroid P of the flexible part 30*b* goes beyond the x-axis, and the Y-coordinate of the centroid P takes a positive value, a cross-section in which the centroid P of the flexible part 30*b* coincides with the axial center G is always generated at a position other than (a) (for example, the centroid P of the flexible part 30*b* is present on the backbone curve B along the axial center G at position (b) or (c) in FIG. 9 (B)). In the cross-section at this position, the second part of the right-hand side of formula 1 is 0; therefore, the geometrical moment of inertia takes the minimum value. As a result, the vicinity of the cross-section (for example, the vicinity of position (b) or (c)) is easily bent locally, and the bending and extending device 1 may have an unexpected shape. In order to prevent such a situation, the bending and extending device 1 of the present embodiment is structured so that a cross-section with the minimum geometrical moment of inertia, which is obtained by formula 1, is not generated.

More specifically, when buckling is generated at a portion of the bending and extending device 1 by the sliding operation of the flexible parts 30*a* and 30*b* so that the cross-section of the buckled portion has a state shown in FIG. 10 (C), in which the contact point T of the second flexible part 30*a* and the inner surface of the guide unit 2 is present on an extending line extending from a line segment connecting the centroid P of the first flexible part 30*b* and the axial center G of the guide unit 2 (corresponding to the y-axis in FIG. 10 (C)), and in which the first flexible part 30*a* and the second flexible part 30*b* are directly or indirectly in contact with each other; and when the cross-section of the buckled portion is divided into two ranges by a predetermined straight line (corresponding to the x-axis in FIG. 10 (C)), the centroid P of the second flexible part 30*b* is not positioned in the range in which the contact point T of the first flexible part 30*a* and the inner surface of the guide unit 2 is present (corresponding to the range above the x-axis).

The predetermined straight line (corresponding to the x-axis in FIG. 10 (C)) refers to a line that passes through the axial center G of the guide unit 2, and orthogonally crosses the extending line (corresponding to the y-axis in FIG. 10 (C)).

Further, the state in which the first flexible part 30*b* and the second flexible part 30*a* are indirectly in contact with each other means that the first flexible part 30*b* and the second flexible part 30*a* are continuously present via a wire or a tube (not shown) that is disposed between them.

In the bending and extending device 1 of the present embodiment having the characteristic structure described above, a cross-section in which the centroid P of the flexible part 30 coincides with the axial center G is not generated in any portion in the longitudinal direction; more specifically, a cross-section in which the geometrical moment of inertia, which is determined by formula 1, takes a minimum value, is not generated. This structure is more specifically described below.

In the bending and extending device 1 of the present embodiment, when the sliding operation of the flexible parts 30*a* and 30*b* is performed, as shown in FIG. 9 (B), the flexible parts 30*a* and 30*b* are bent, and the interval between the flexible parts 30*a* and 30*b* becomes different in each position in the longitudinal direction. At this point, the cross-section in which the first flexible part 30*b* and the second flexible part 30*a* are in contact with each other, and the second flexible part 30*a* is in contact with the inner surface of the guide unit 2 (i.e., the cross-section in which the flexible parts 30*a* and 30*b* are buckled), as shown in the cross-section shown in FIG. 10 (*c*) (the cross-section at the position (a) in FIG. 9), may be regarded as a cross-section in which the first flexible part 30*b* and the second flexible part 30*a* are closest. Further, in the bending and extending device 1 of the present embodiment, when the cross-section in which the flexible parts 30*a* and 30*b* are closest is divided into two ranges by the x-axis (corresponding to the predetermined straight line), the centroid P of the first flexible part 30*b* is not positioned in the range in which the contact point T of the second flexible part 30*a* and the guide unit 2 is present (corresponding to the range above the x-axis). More specifically, the centroid P of the first flexible part 30*b* is positioned in the range in which the contact point T is not present (the range below the x-axis). More specifically, the centroid P of the flexible part 30b is always positioned in the range in which the contact point T is not present (corresponding to the range below the x-axis) in cross-sections of other positions, as well. As shown above, the bending and extending device 1 of the present embodiment does not have a cross-section in which the centroid P of the flexible part 30b coincides with the axial center G (more specifically, the bending and extending device 1 of the present embodiment does not have a cross-section in which the geometrical moment of inertia, which is determined by formula 1, takes a minimum value). The structure of the bending and extending device 1 of the present embodiment is thus advantageous in terms of preventing unexpected local bending due to buckling.

Although the above explanation describes, according to FIG. 10 (C), the flexible part 30b as the first flexible part and the flexible part 30a as the second flexible part, for easy understanding of the structure of the bending and extending device 1, this structure is merely an example; the second flexible part refers to a flexible part 30, i.e., one of the flexible parts 30a and 30b, which is in contact with the inner surface of the guide unit 2, and the first flexible part refers to another flexible part 30, i.e., the other one of the flexible parts 30a and 30b, which is in contact with the second flexible part either directly or indirectly (more specifically, it is also possible that the flexible part 30a corresponds to the first flexible part, and that the flexible part 30b corresponds to the second flexible part). The cross-sectional shape of the guide unit 2 approximates the shape of the perpendicular cross-section of the guide unit 2, and the cross-sectional shape of the flexible parts 30a and 30b approximates the perpendicular cross-section of the flexible parts 30a and 30b. Such cross-section forms may be obtained from drawings upon designing, or from Computer-Aided Design (CAD) data.

Further, the characteristics of the structure of the bending and extending device 1 described above is not made in light of the change in shape of the cross-section of the flexible parts 30a and 30b, and the guide unit 2, by an external force such as a pulling force. The determination as to whether the bending and extending device has the above structure of the bending and extending device 1 is carried out by obtaining image data of a cross-section shown in FIG. 10 (C) (i.e., the cross-section in which the contact point T of the second flexible part 30 and the inner surface of the guide unit 2 is present on an extending line extending from a line segment connecting the centroid P of the first flexible part 30 and the axial center G of the guide unit 2, and in which the first flexible part 30 and the second flexible part 30 are directly or indirectly in contact with each other) by CAD, CT scanning, or the like on the assumption that the cross-sectional shape of the guide unit 2 is maintained as a circular shape and the cross-sectional shape of the flexible parts 30a and 30b is maintained as a semicircular shape, even when an external force is applied; and determining that whether the centroid P of the second flexible part 30 is positioned in the range in which the contact point T of the first flexible part 30 and the guide unit 2 is present (corresponding to the range below the x-axis), by referring to the cross-section shown in the image data.

Further, the bending and extending device 1 of the present embodiment is capable of maintaining a desired bending form because of the structural characteristics of the movable part 3, even when the bending and extending device 1 is inserted into a body as a movable catheter, and a large external force is applied to the guide unit 2 due to the contact with a vascular wall or organ. More specifically, in the bending and extending device 1 of the present embodiment, as described above, the shape of the cross-section of the flexible parts 30a and 30b corresponds to a semicircular plane obtained by equally dividing the internal cross-section of the guide unit 2 into two planes. Further, in a state in which the flexible parts 30a and 30b are positioned in the guide unit 2, the shape of the combination of the cross-sections of the flexible parts 30a and 30b substantially coincides with the circular shape of the internal cross-section of the guide unit 2. Therefore, gap S (FIG. 3) between the flexible parts 30a and 30b, and the guide unit 2; and distance D (FIG. 3) between the flexible parts 30a and 30b can be sufficiently reduced. Thus, even if a large external force applied to the guide unit 2 is transmitted to the flexible parts 30a and 30b through the guide unit 2, the flexible parts 30a and 30b are prevented from being largely deformed due to buckling. This prevents the guide unit 2 from being greatly bent halfway through the operation, or prevents generation of unexpected deformation in the guide unit 2 due to buckling of the flexible parts 30a and 30b. Therefore, even when a large external force is applied to the guide unit 2, it is possible to maintain a desired bending form.

Furthermore, in the state in which the flexible parts 30a and 30b are positioned in the guide unit 2, since the side surface 33a of the flexible part 30a becomes parallel with the side surface 33b of the opposed flexible part 30b, the flexible parts 30a and 30b are prevented from being twisted or crossed, even when the bending and extending device 100 is long (for example, the length is about 1500 nut). Therefore, the sliding operation of the flexible parts 30a and 30b may be smoothly performed, and the bending and extending device 1 can be bent into a desired shape.

Further, the bending and extending device 1 of the present embodiment has a significantly small number of component parts, thus enabling conversion and transmission of the power of flexible deformation with a simple structure. Therefore, the bending and extending device 1 makes it possible to improve safety, reduce the production cost, and increase or decrease the device diameter (structural scalability). Further, when the bending and extending device 1 is applied as a medical device such as a surgical instrument or endoscope, the required sterilization and disinfection can be easily performed.

Further, in the bending and extending device 1, the deformation form of the guide unit 2 and the force to maintain the form of the deformed guide unit 2 depend on the relative rigidity between the movable part 3 and the guide unit 2. As described above, by determining the material and geometric parameters (thickness, width, length) of the movable part 3 and the guide unit 2 so that the rigidity of the movable part 3 becomes equal to or greater than the rigidity of the guide unit 2, it is possible to ensure a desired deformation form of the guide unit 2 while maintaining the form of the deformed guide unit 2.

Further, when the guide unit 2 is formed from β titanium or nickel titanium, since the β titanium and the nickel titanium has high resilience, it is possible to return the guide unit 2 to the initial form by returning the proximal end 32 of the flexible part 30 that was slid to the initial position, or by sliding a proximal end 32 of the flexible part 30 that was not slid.

Further, when the guide unit 2 is formed from p titanium, which is a nonmagnetic material, the bending and extending device 1 of the present embodiment may be used as an elastic body for a surgical instrument, an endoscope, or the like used under the MR conditions.

The present invention is not limited to the embodiment described above, and may be altered in various ways within the scope of the claims.

Figure 11:
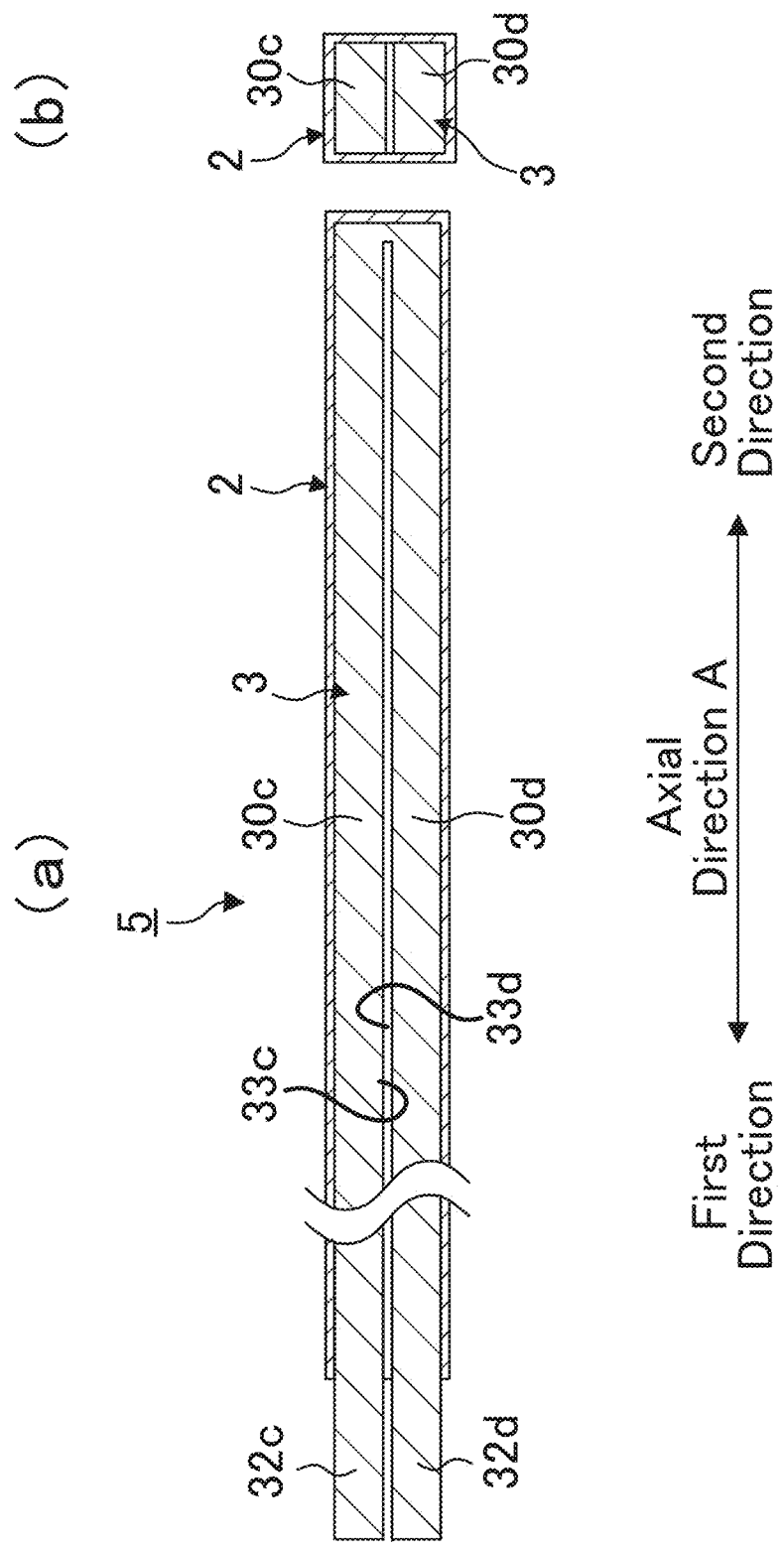
FIG. 11: (a) is a vertical cross-sectional view corresponding to FIG. 2 (a), showing a modification example of a bending and extending device; and (b) is a horizontal cross-sectional view corresponding to FIG. 2 (b), showing a modification example of a bending and extending device.
Figure 12:
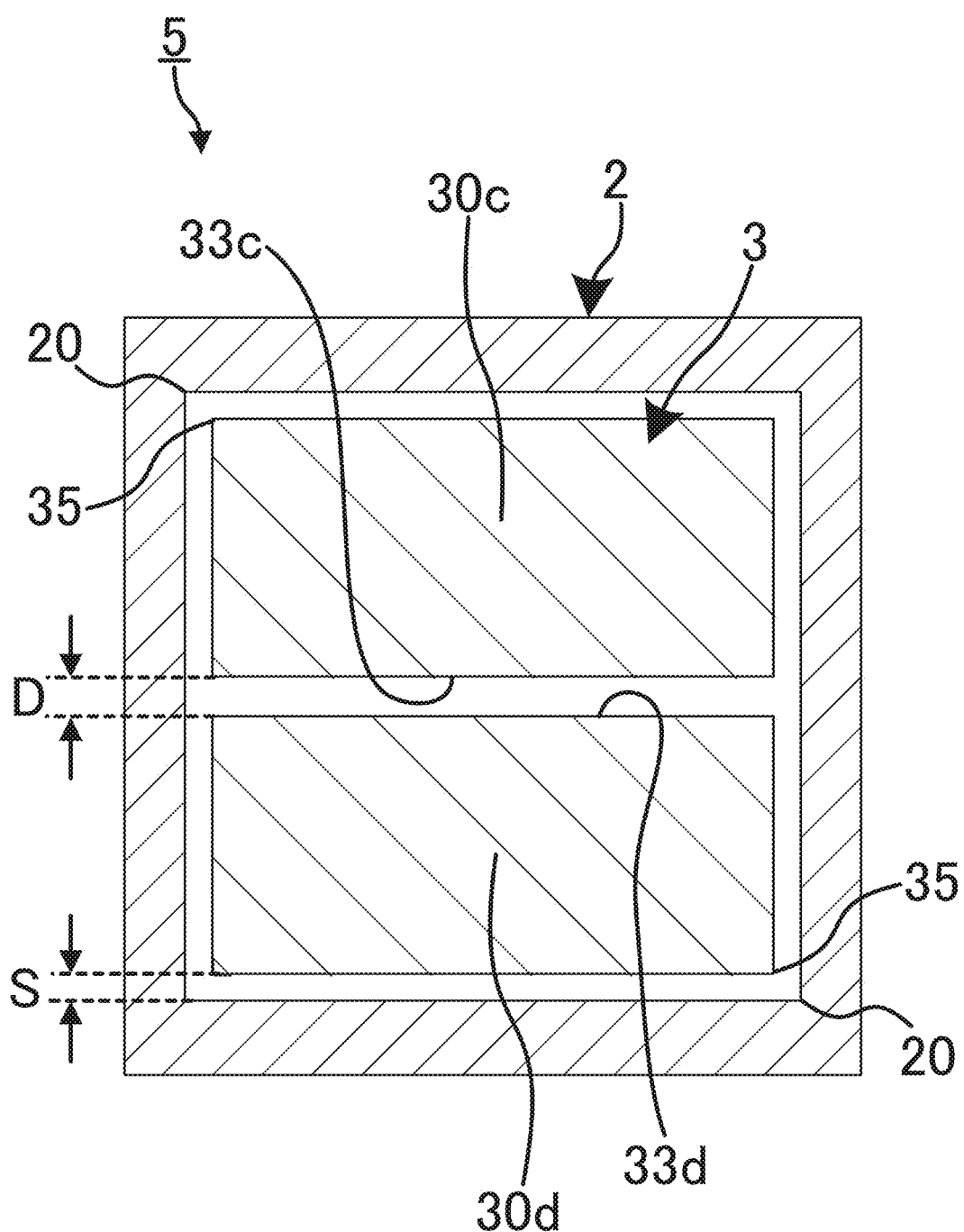
FIG. 12 is a magnified view of FIG. 11 (b).

For example, the bending and extending device of the present invention may be altered as shown in FIGS. 11 and 12. FIG. 11 (a) is a vertical cross-sectional view corresponding to FIG. 2 (a), showing a modification example of the bending and extending device. FIG. 11 (b) is a horizontal cross-sectional view corresponding to FIG. 2 (b), showing a bending and extending device according to a modification example (in FIG. 9, some portions of the bending and extending device are omitted). FIG. 12 is a magnified view of FIG. 11 (b).

In the bending and extending device 5 shown in FIG. 11 or 12, the internal cross-section of the guide unit 2 has a rectangular shape. The movable part 3 is constituted, either partially or entirely, of two belt-like flexible parts 30c and 30d that extend in the axial direction of the guide unit 2. The two flexible parts 30c and 30d are connected at their ends. The flexible parts 30c and 30d have a cross-sectional shape corresponding to one of the rectangular planes obtained by equally dividing the internal cross-section of the guide unit 2 into two planes.

Further, in a state in which the movable part 3 is inserted into the guide unit 2, and the flexible parts 30c and 30d are positioned in the guide unit 2, the shape of the combination of the cross-sections of the flexible parts 30c and 30d substantially coincides with the rectangular shape of the internal cross-section of the guide unit 2. Therefore, the gap S between the flexible parts 30c and 30d, and the guide unit 2; and the distance D between the flexible parts 30c and 30d are reduced. Further, the side surface 33c of the flexible part 30c, and the side surface 33d of the flexible part 30d opposite to the side surface 33c both form a plane extending in the axial direction A of the guide unit 2 (FIG. 4); and become parallel to each other. Further, the proximal ends 32c and 32d of the flexible parts 30c and 30d are extended to the outside of the guide unit 2.

As with the bending and extending device 1 shown in FIG. 1, 2, or the like, the bending and extending device 5 shown in FIG. 11 or 12 also has an advantageous structure in terms of preventing unexpected local bending due to buckling. More specifically, when a cross-section in which, as shown in FIG. 13, the contact point T of the second flexible part 30c and the inner surface of the guide unit 2 is present on a line extending from a line segment connecting the centroid P of the first flexible part 30d and the axial center G of the guide unit 2 (corresponding to the y-axis in FIG. 13), and in which the first flexible part 30d and the second flexible part 30c are directly or indirectly in contact with each other, is generated at a portion in the longitudinal direction of the bending and extending device 5 by bending or extending the bending and extending device 5 by the sliding operation of the flexible parts 30c and 30d; and when the cross-section is divided into two ranges by a predetermined straight line (corresponding to the x-axis in FIG. 13), the centroid P of the second flexible part 30d is not positioned in the range in which the contact point T of the first flexible part 30c and the inner surface of the guide unit 2 is present (corresponding to the range above the x-axis).

Figure 13:
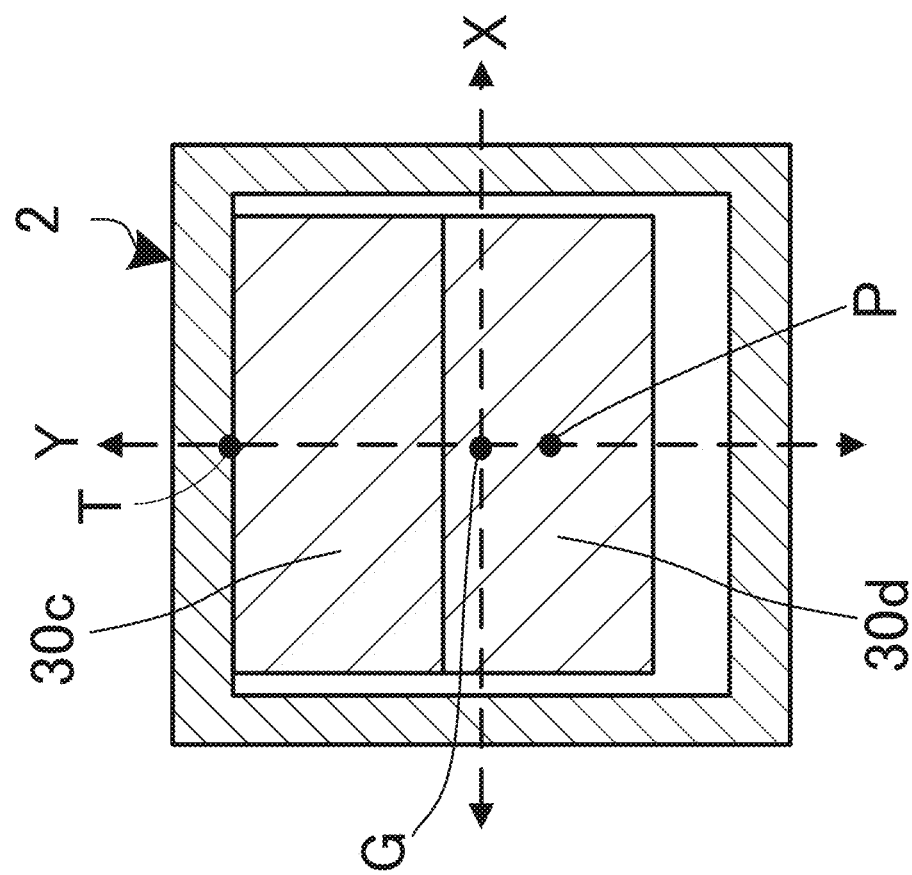
FIG. 13 is a cross-sectional view showing a state in which a flexible part is buckled.

The predetermined straight line (the x-axis in FIG. 13) refers to a line that passes through the axial center G of the guide unit 2, and orthogonally crosses the extending line (the y-axis in FIG. 13).

Further, the state in which the first flexible part 30d and the second flexible part 30c being indirectly in contact with each other means that the first flexible part 30d and the second flexible part 30c are continuously present via a wire or a tube (not shown) that is disposed between them.

With the characteristics described above, the bending and extending device 5 does not have a cross-section in which the centroid P of the flexible part 30 coincides with the axial center G of the guide unit 2 in any portion in the longitudinal direction. Therefore, the bending and extending device 5 has an advantageous structure in terms of preventing unexpected local bending due to buckling.

Although the above explanation describes, according to FIG. 13, the flexible part 30d as the first flexible part and the flexible part 30c as the second flexible part, for easy understanding of the structure of the bending and extending device 5, this structure is merely an example. Among the flexible parts 30c and 30d, a flexible part 30 in contact with the inner surface of the guide unit 2 corresponds to the second flexible part, and the other flexible part 30 in contact with the second flexible part 30 either directly or indirectly corresponds to the first flexible part (in contrast to the above example, it is also possible that the flexible part 30c corresponds to the first flexible part, and that the flexible part 30d corresponds to the second flexible part).

Further, in the bending and extending device 5 shown in FIG. 11 or 12, the corner portion 35 of the flexible part 30 and the corner portion 20 of the guide unit 2 are engaged, thereby stabilizing the direction of the flexible parts 30c and 30d; therefore, the flexible parts 30c and 30d are prevented from being twisted or crossed.

Figure 14:
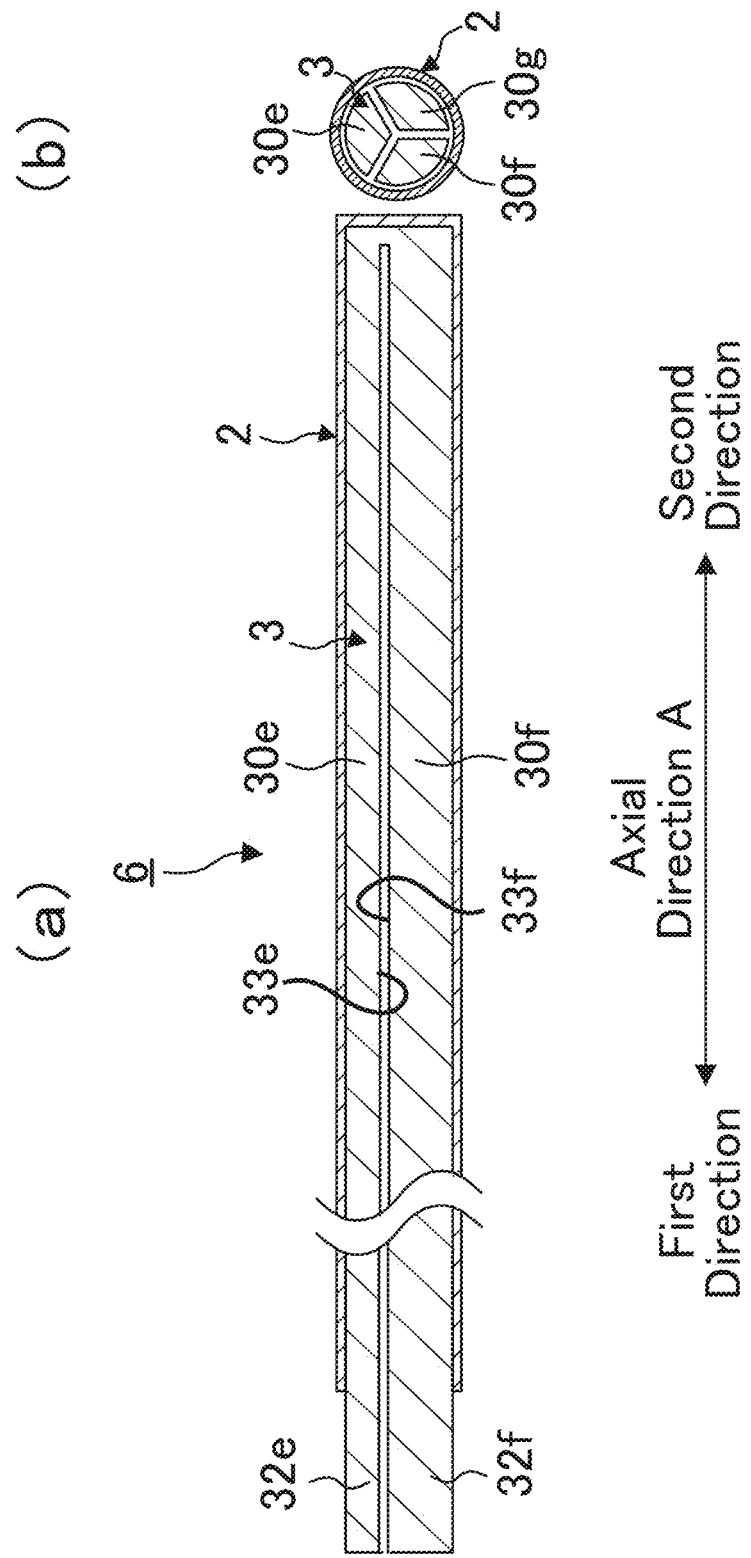
FIG. 14: (a) is a vertical cross-sectional view corresponding to FIG. 2 (a), showing a modification example of a bending and extending device; and (b) is a horizontal cross-sectional view corresponding to FIG. 2 (b), showing a modification example of a bending and extending device.
Figure 15:
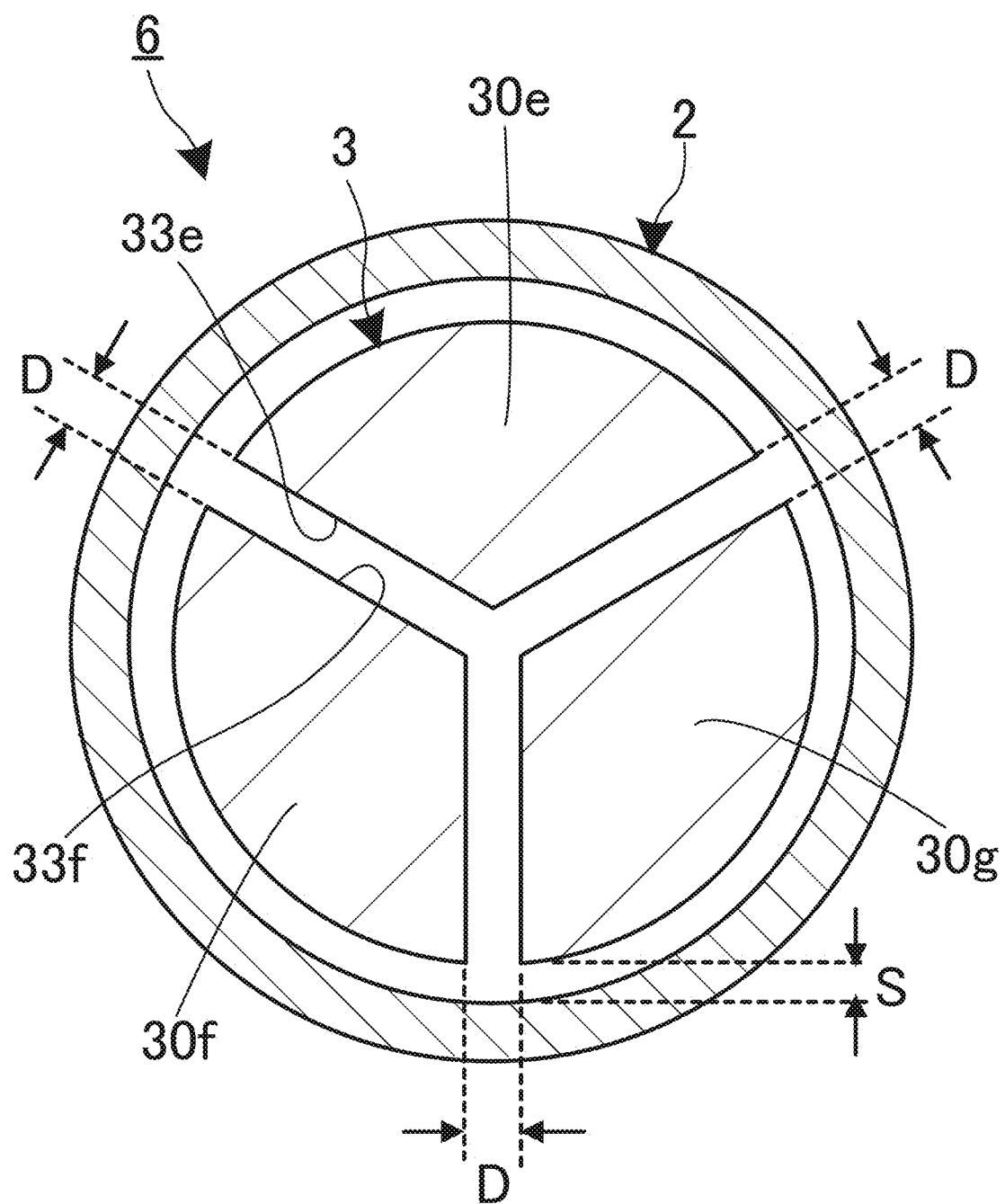
FIG. 15 is a magnified view of FIG. 14 (b).

Further, the bending and extending device of the present invention may also be altered as shown in FIGS. 14 and 15. FIG. 14 (a) is a vertical cross-sectional view corresponding to FIG. 2 (a), showing a modification example of the bending and extending device. FIG. 14 (b) is a horizontal cross-sectional view corresponding to FIG. 2 (b), showing a bending and extending device 6 according to a modification example (in FIG. 14, some portions of the bending and extending device 6 are omitted). FIG. 15 is a magnified view of FIG. 14 (b).

In the bending and extending device 6 shown in FIG. 14 or 15, the internal cross-section of the guide unit 2 has a circular shape. The movable part 3 is constituted, either partially or entirely, of three belt-like flexible parts 30e, 30f, and 30g that extend in the axial direction A of the guide unit 2. The three flexible parts 30e, 30f, and 30g are connected at their ends. The flexible parts 30e, 30f, and 30g have a cross-sectional shape corresponding to one of the fan-shaped planes obtained by equally dividing the internal cross-section of the guide unit 2 into three planes. Further, in a state in which the movable part 3 is inserted into the guide unit 2 so that the flexible parts 30e, 30f, and 30g are positioned in the guide unit 2, the shape of the combination of the cross-sections of the flexible parts 30e, 30f, and 30g substantially coincides with the circular shape of the internal cross-section of the guide unit 2, and the side surface 33 of the first flexible part 30 and the side surface 33 of the second flexible part 30 opposite thereto both form a plane extending in the axial direction A of the guide unit 2; and become parallel to each other. (For example, the side surface 33e of the flexible part 30e and the side surface 33f of the flexible part 30f opposite to the side surface 33e extend in the axial direction A, and become parallel to each other.) Further, the proximal end 32 of the flexible part 30 is extended to the outside of the guide unit 2 (although FIG. 14 shows a state in which the proximal ends 32e and 32f of the flexible parts 30*e* and 30*f* are extended to the outside of the guide unit 2, the proximal end (not shown) of the flexible part 30*g* is also extended to the outside of the guide unit 2).

Figure 16:
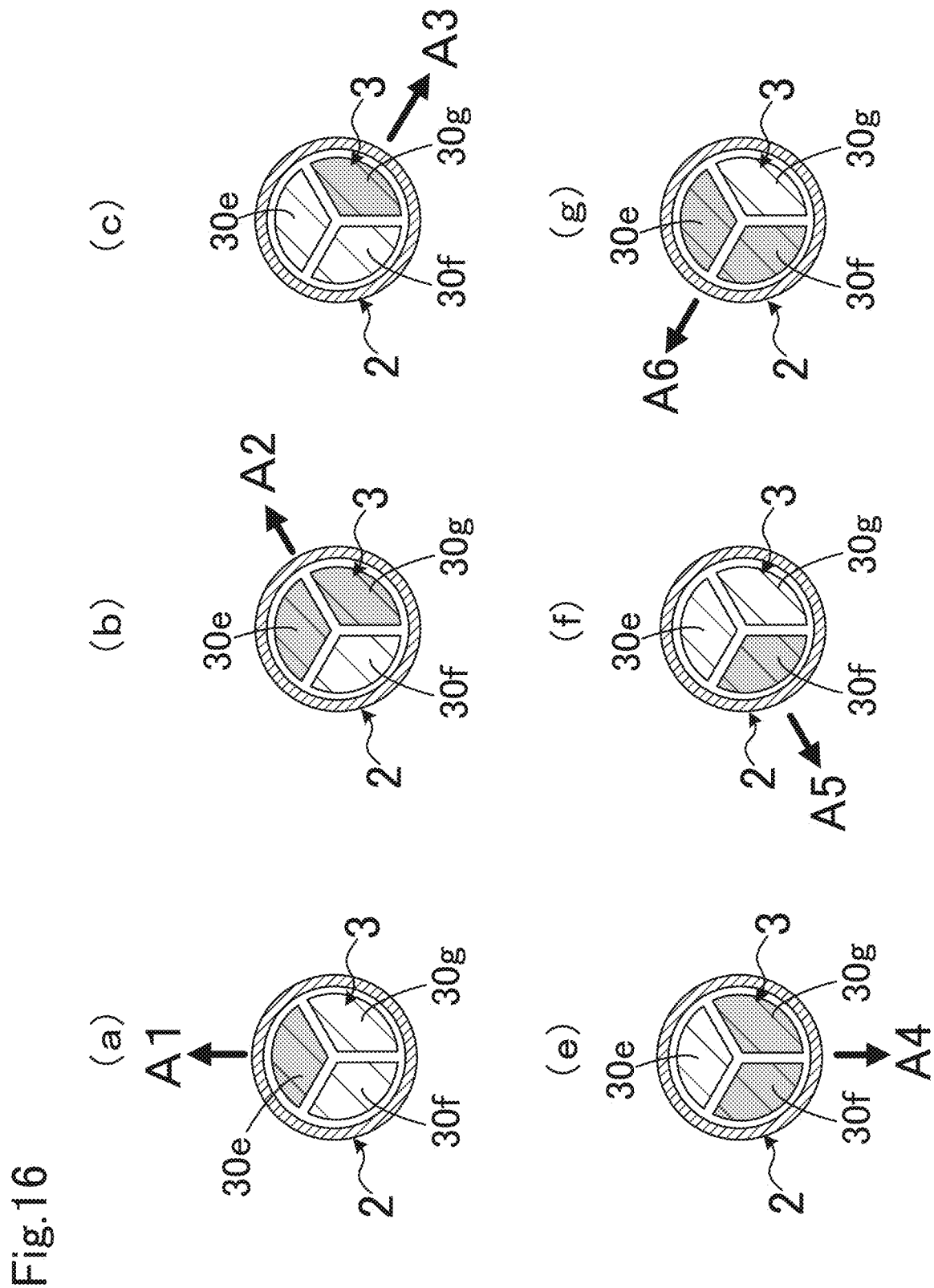
FIG. 16 is a cross-sectional view showing the bending direction of a bending and extending device of a modification example.

The bending and extending device 6 shown in FIGS. 14 and 15 appropriately selects one of the flexible parts 30 for performing the sliding operation, thereby enabling bending in the six directions A1 to A6 shown in FIG. 16 (in FIG. 16, the flexible parts 30 that perform the sliding operation are colored). All of the directions A1 to A6 are perpendicular to the axial direction A, and their inclinations vary on a 60-degree basis in the circumference of the guide unit 2. For example, when the proximal end 32*e* of the flexible part 30*e* is made to slide in one side in the axial direction A of the guide unit 2, the device 6 can be bent in the direction A1 shown in FIG. 16 (*a*). Further, when the proximal end 32*e* of the flexible part 30*e* and the proximal end 32*f* of the flexible part 30*f* are made to slide together in one side in the axial direction A of the guide unit 2, the device 6 can be bent in the direction A6 shown in FIG. 16 (*g*). More specifically, the directions A1 to A6 designate relative directions of the flexible part 30 that performs a sliding operation, and the other flexible parts 30. For example, the direction A1 designates a relative direction of the flexible part 30*e* that performs a sliding operation, and other flexible parts 30*f* and 30*g* (more specifically, A1 is the relative direction of the cross-section of the flexible part 30*e*, and the combined range of the cross-sections of the flexible parts 30*f* and 30*g*). Further, the direction A6 designates a relative direction of the flexible parts 30*e* and 30*f* that perform a sliding operation, and the other flexible part 30*g* (more specifically, AG is the relative direction of the combined range of the cross-sections of the flexible parts 30*e* and 30*f*, and the cross-section of the flexible part 30*g*).

The bending and extending device 6 described above is capable of causing bending in any vertical and horizontal direction from the axial center without solely rotating the movable part 3 about the axis, or rotating the pair of the movable part 3 and the guide unit 2 about the axis. Therefore, when the bending and extending device 6 is a microcatheter, which has a long and narrow shape and is relatively soft, and the torque thus cannot be sufficiently transmitted to the distal end side after a rotational axial force is applied to the movable part 3 and the guide unit 2, it is possible to cause bending in various directions.

Further, the bending and extending device 6 shown in FIG. 14 or 15 also has an advantageous structure in terms of preventing unexpected local bending due to buckling. More specifically, when a cross-section in which, as shown in FIG. 17, the contact point T of the second flexible part 30*e* or 30*g* and the inner surface of the guide unit 2 is present on an extending line extending from a line segment connecting the centroid P of the first flexible part 30*f* and the axial center G of the guide unit 2 (corresponding to the y-axis in FIG. 17), and in which the first flexible part 30*a* and the second flexible part 30*e* or 30*g* are directly or indirectly in contact with each other, is generated at a portion in the longitudinal direction of the bending and extending device 6 by bending and extending the bending and extending device 6 by the sliding operation of the flexible parts 30*c* and 30*d*; and when the cross-section is divided into two ranges by a predetermined straight line (corresponding to the x-axis in FIG. 17), the centroid P of the first flexible part 30*f* is not positioned in the range in which the contact point T of the second flexible part 30*e* or 30*g* and the inner surface of the guide unit 2 is present (corresponding to the range above the x-axis).

Figure 17:
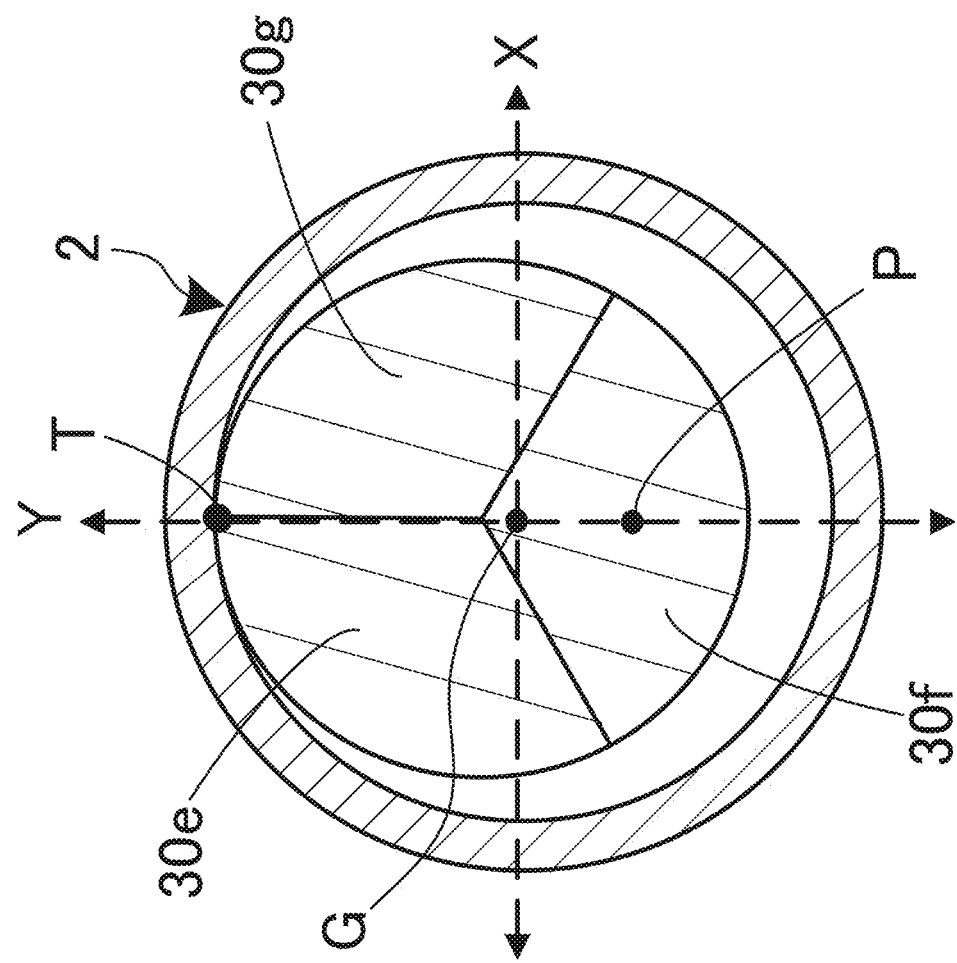
FIG. 17 is a cross-sectional view showing a state in which a flexible part is buckled.

The predetermined straight line (the x-axis in FIG. 17) refers to a line that passes through the axial center G of the guide unit 2, and orthogonally crosses the extending line (the y-axis in FIG. 17).

Further, the state in which the first flexible part 30*f* and the second flexible part 30*e* or 30*g* being indirectly in contact with each other means that the first flexible part 30*f* and the second flexible part 30*e* or 30*g* are continuously present via a wire or a tube (not shown) that is disposed between them.

With the characteristics described above, the bending and extending device 6 does not have a cross-section in which the centroid P of the flexible part 30 coincides with the axial center G in any portion in the longitudinal direction. Therefore, the bending and extending device 6 has an advantageous structure in terms of preventing unexpected local bending due to buckling.

Although the above explanation describes, according to FIG. 17, the flexible part 30*f* as the first flexible part and the flexible part 30*e* or 30*g* as the second flexible part, for easy understanding of the structure of the bending and extending device 6, this structure is merely an example. Among the flexible parts 30*e*, 30*f*, and 30*g*, a flexible part 30 in contact with the inner surface of the guide unit 2 corresponds to the second flexible part, and other flexible parts 30 in contact with the second flexible part 30 either directly or indirectly correspond to the first flexible part.

Furthermore, in the bending and extending device 6 shown in FIG. 14 and FIG. 15, as described above, the shape of the cross-section of the flexible parts 30*e*, 30*f*, and 30*g* corresponds to one of the fan-shaped planes obtained by equally dividing the internal cross-section of the guide unit 2. Further, with the state in which the combination of the cross-sections of the flexible parts 30*e*, 30*f*, and 30*g* substantially coincides with the circular shape of the internal cross-section of the guide unit 2, the gap S (FIG. 15) between the flexible parts 30*e*, 30*f*, and 30*g*, and the guide unit 2; and the distance D (FIG. 15) between two adjacent flexible parts 30 are reduced. Thus, even if a large external force is transmitted to the flexible parts 30*e*, 30*f*, and 30*g* through the guide unit 2, each flexible part 30 is prevented from buckling. This prevents the guide unit 2 from being largely bent halfway through the operation; or prevents generation of unexpected deformation in the guide unit 2, thereby maintaining the desired bending form.

Furthermore, in the state in which the flexible parts 30*e*, 30*f*, and 30*g* are positioned in the guide unit 2, since the side surface 33 of the first flexible part 30 becomes parallel to the side surface 33 of another flexible part 30 opposite thereto, the first flexible part 30 and the other flexible parts 30 are prevented from being twisted or crossed (for example, since the side surfaces 33*e* and 33*f* of the first flexible parts 30*e* and 33*f* become parallel, the flexible parts 30*e* and 30*f* are prevented from being twisted or crossed). Therefore, the sliding operation of the flexible parts 30*e*, 30*f*, and 30*g* may be smoothly performed, and the bending and extending device 6 can be bent into a desired shape.

Figure 18:
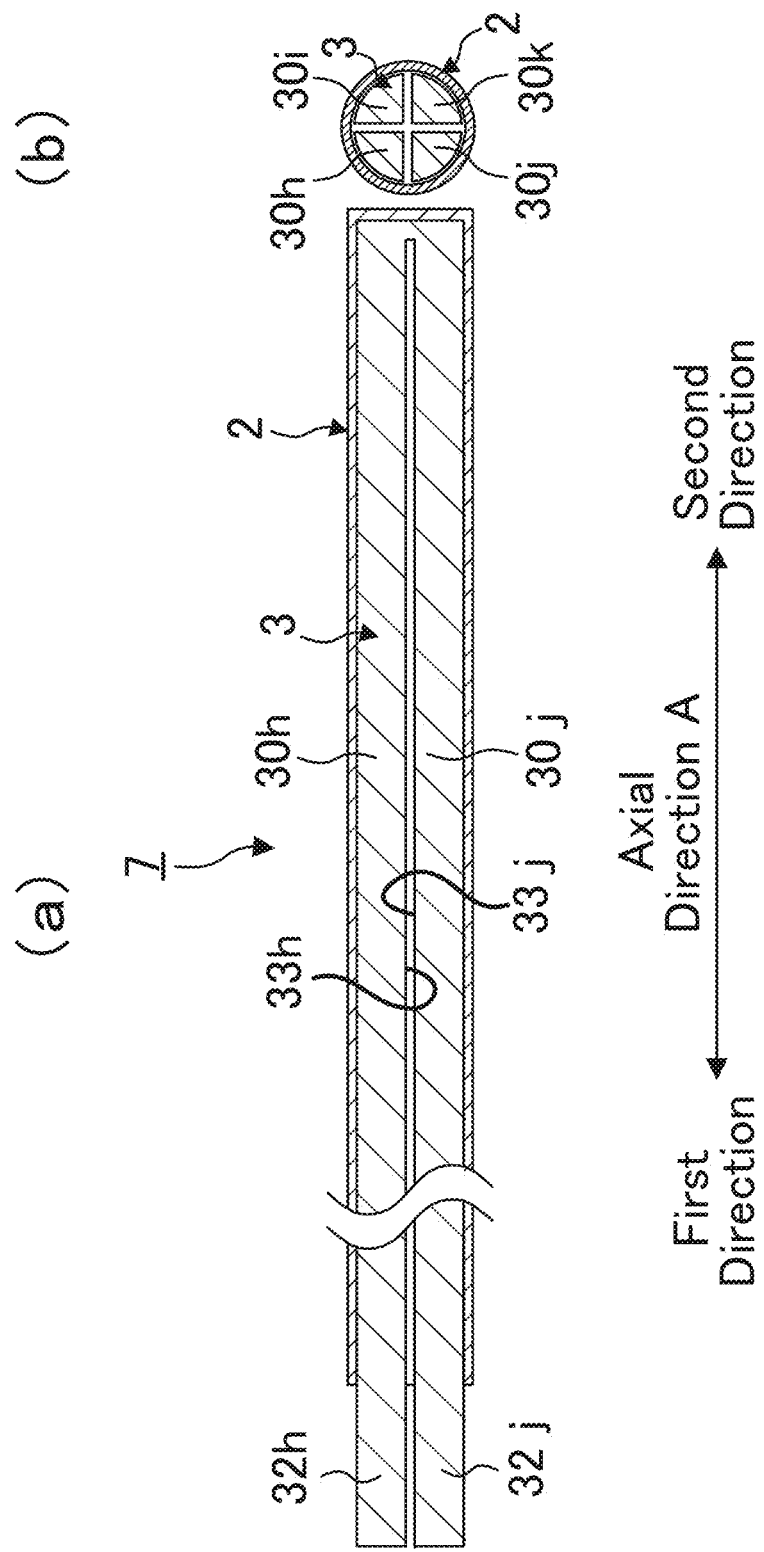
FIG. 18: (a) is a vertical cross-sectional view corresponding to FIG. 2 (a), showing a modification example of a bending and extending device; and (b) is a horizontal cross-sectional view corresponding to FIG. 2 (b), showing a modification example of a bending and extending device.
Figure 19:
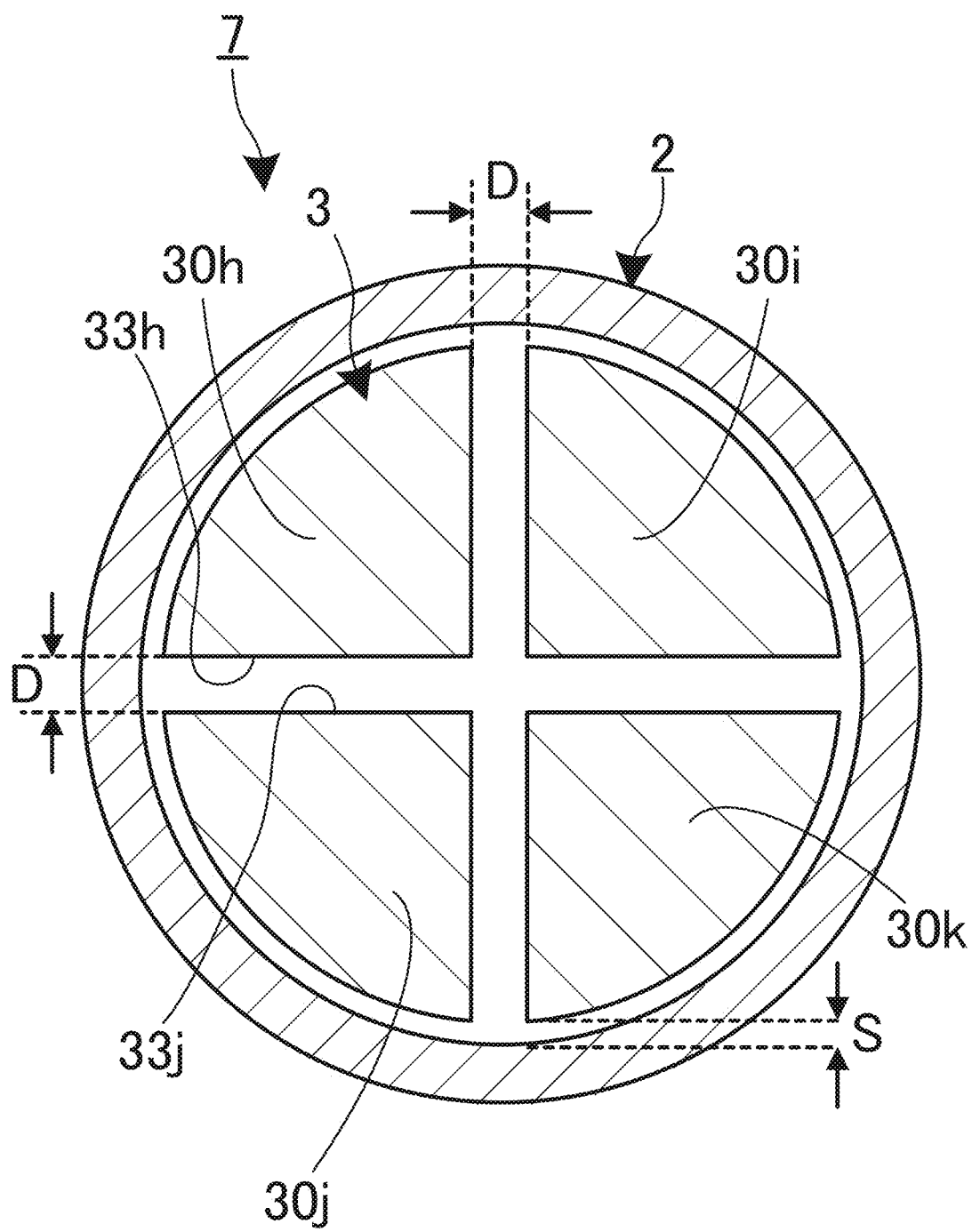
FIG. 19 is a magnified view of FIG. 18 (b).

Further, the bending and extending device of the present invention may also be altered as shown in FIGS. 18 and 19. FIG. 18 (*a*) is a vertical cross-sectional view corresponding to FIG. 2 (*a*), showing a bending and extending device 7 according to a modification example. FIG. 18 (*b*) is a horizontal cross-sectional view corresponding to FIG. 2 (*b*), showing a bending and extending device 7 according to a modification example (in FIG. 18, some portions of the bending and extending device 7 are omitted). FIG. 19 is a magnified view of FIG. 18 (*b*).

In the bending and extending device 7 shown in FIG. 18 or 19, the internal cross-section of the guide unit 2 has a circular shape. The movable part 3 is constituted, either partially or entirely, of four belt-like flexible parts 30h, 30i, 30j, and 30k that extend in the axial direction A of the guide unit 2. The four flexible parts 30h, 30i, 30j, and 30k are connected at their ends. The flexible parts 30h, 30i, 30j, and 30k have a cross-sectional shape corresponding to one of the fan-shaped planes obtained by equally dividing the internal cross-section of the guide unit 2 into four planes. Further, in a state in which the movable part 3 is inserted into the guide unit 2 so that the flexible parts 30h, 30i, 30j, and 30k are positioned in the guide unit 2, the shape of the combination of the cross-sections of the flexible parts 30h, 30i, 30j, and 30k substantially coincides with the circular shape of the internal cross-section of the guide unit 2, and the side surface 33 of the first flexible part 30 and the side surface 33 of the second flexible part 30 opposite thereto both form a plane extending in the axial direction A of the guide unit 2; and become parallel to each other (for example, the side surface 33h of the flexible part 30h and the side surface 33j of the flexible part 30j opposite to the side surface 33h extend in the axial direction A, and become parallel to each other). Further, the proximal end 32 of each flexible part 30 is extended to the outside of the guide unit 2 (although FIG. 18 shows a state in which the proximal ends 32h and 32j of the flexible parts 30h and 30j are extended to the outside of the guide unit 2, the proximal ends (not shown) of the flexible parts 30i and 30k are also extended to the outside of the guide unit 2).

Figure 20:
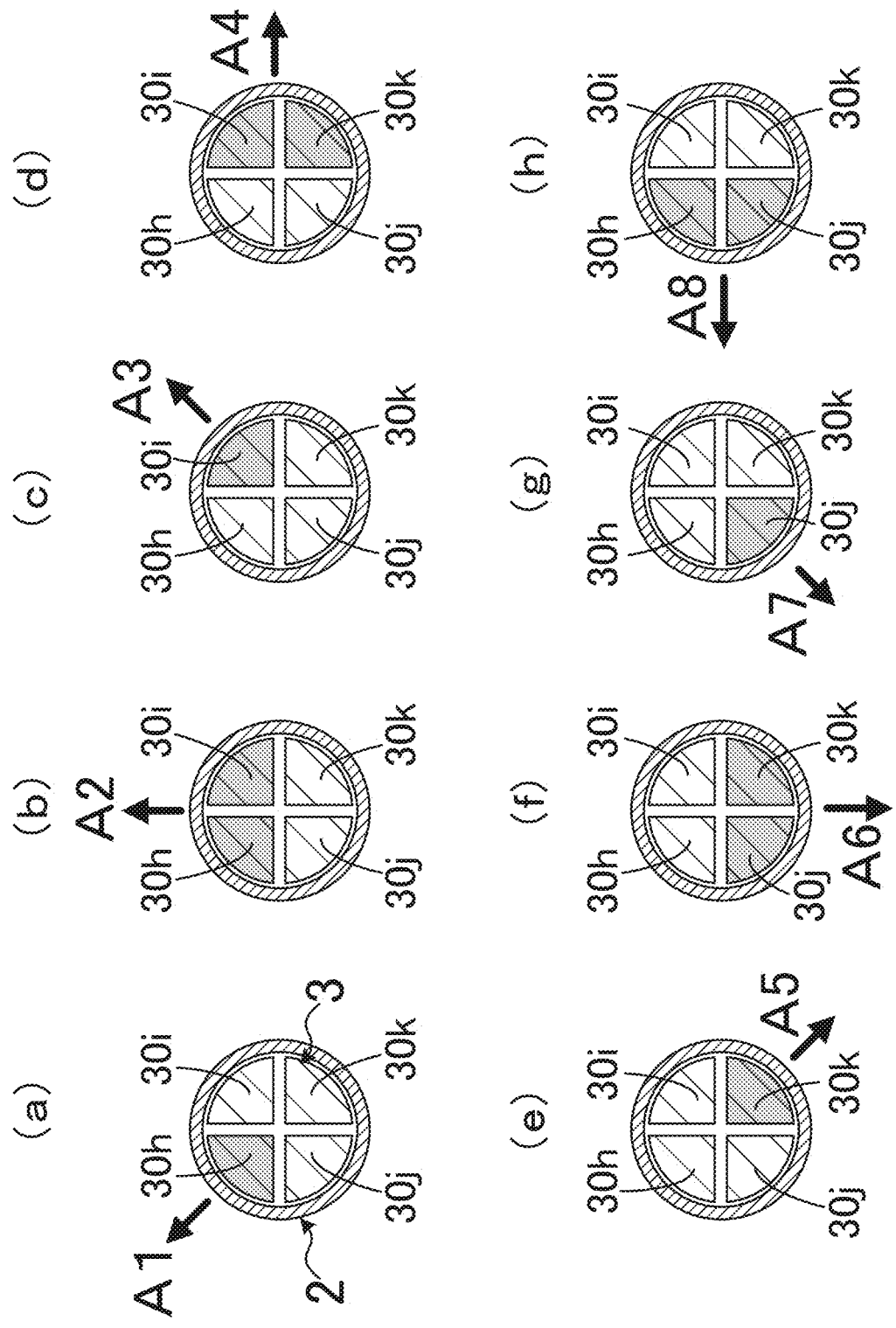
FIG. 20 is a cross-sectional view showing the bending direction of a bending and extending device of a modification example.

The bending and extending device 7 shown in FIGS. 18 and 19 appropriately selects one of the flexible parts 30 for performing the sliding operation, thereby enabling bending in the eight directions A1 to A8 shown in FIG. 20 (in FIG. 20, the flexible parts 30 that perform the sliding operation are colored). All of the directions A1 to A8 are perpendicular to the axial direction A, and their inclinations vary on a 45-degree basis in the circumference of the guide unit 2. For example, when the proximal end 32h of the flexible part 30h is made to slide in one side in the axial direction A of the guide unit 2, the device 7 can be bent in the direction A1 shown in FIG. 20 (a). Further, when the proximal end 32h of the flexible part 30h and the proximal end 32j of the flexible part 30j are made to slide together in one side in the axial direction A of the guide unit 2, the device 7 can be bent in the direction A8 shown in FIG. 20 (h). More specifically, the directions A1 to A8 designate relative directions of the flexible part 30 that performs a sliding operation, and the other flexible parts 30. For example, the direction A1 designates a relative direction of the flexible part 30h that performs a sliding operation, and other flexible parts 30i, 30j, and 30k (more specifically, A1 is the relative direction of the cross-section of the flexible part 30h, and the combined range of the cross-sections of the flexible parts 30i, 30j, and 30k). Further, the direction A8 designates a relative direction of the flexible parts 30h and 30j that perform a sliding operation, and other flexible parts 30i and 30k (more specifically, A1 is the relative direction of the combined range of the cross-sections of the flexible parts 30h and 30j and the combined range of the cross-sections of the flexible parts 30i and 30k).

The bending and extending device 7 described above is capable of causing bending in eight vertical and horizontal directions from the axial center, without rotating the movable part 3 (the flexible parts 30e, 30f, and 30g) or the guide unit 2 about the axis. Therefore, when the bending and extending device 7 is long and narrow and is relatively soft, and the torque thus cannot be sufficiently transmitted to the distal end side, it is possible to cause bending in various directions.

Further, the bending and extending device 7 shown in FIG. 18 or 19 also has an advantageous structure in terms of preventing unexpected local bending due to buckling. More specifically, when a cross-section in which, as shown in FIG. 21, the contact point T of the second flexible part 30h and the inner surface of the guide unit 2 is present on an extending line extending from a line segment connecting the centroid P of the first flexible part 30k and the axial center G of the guide unit 2 (corresponding to the y-axis in FIG. 21), and in which the first flexible part 30k and the second flexible part 30h are directly or indirectly in contact with each other, is generated at a portion in the longitudinal direction of the bending and extending device 7 by bending and extending the bending and extending device 7 by the sliding operation of the flexible parts 30h, 30i, 30j, and 30k; and when the cross-section is divided into two ranges by a predetermined straight line (corresponding to the x-axis in FIG. 21), the centroid P of the first flexible part 30k is not positioned in the range in which the contact point T of the second flexible part 30h and the inner surface of the guide unit 2 is present (corresponding to the range above the x-axis).

Figure 21:
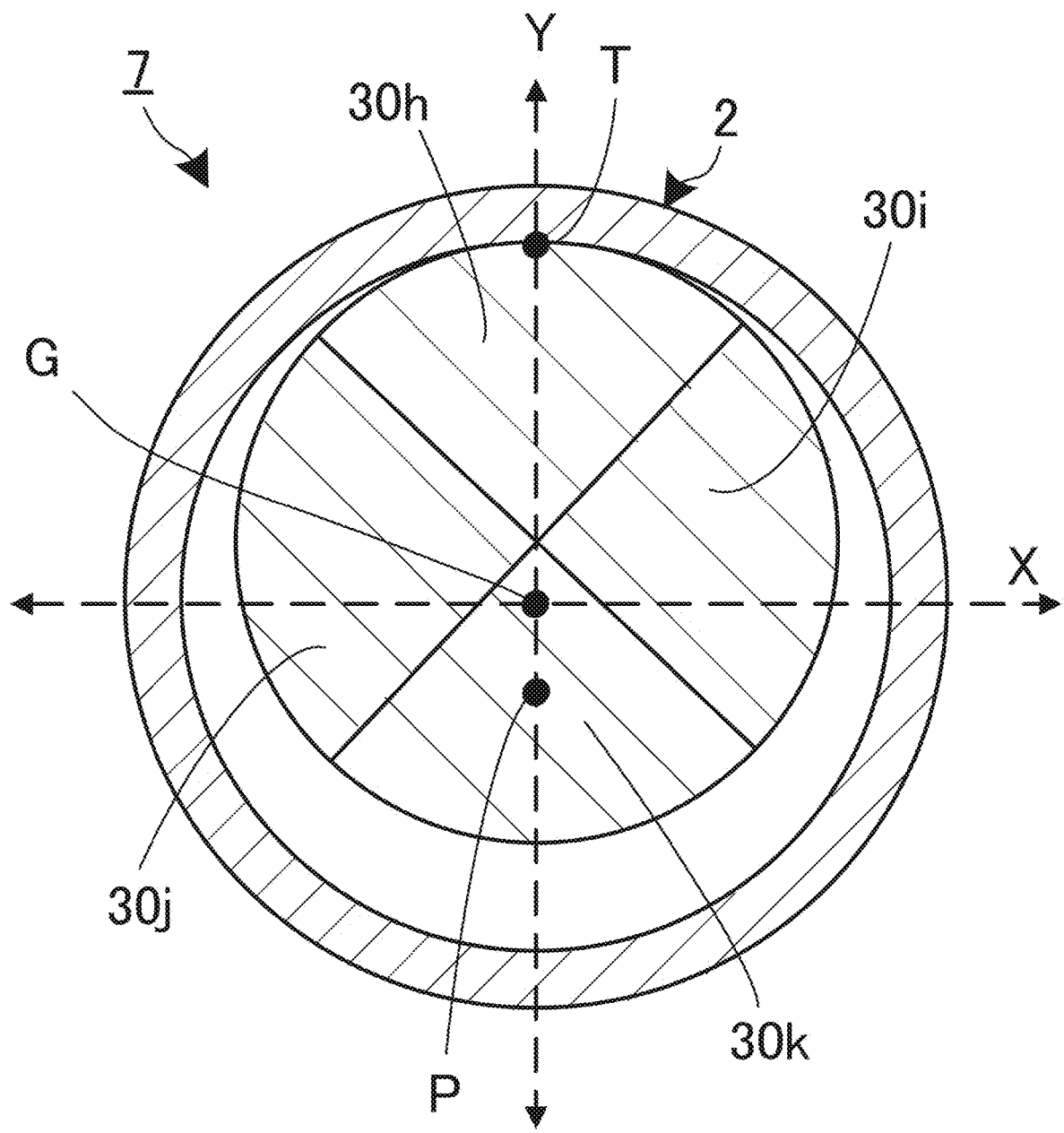
FIG. 21 is a cross-sectional view showing a state in which a flexible part is buckled.

The predetermined straight line (the x-axis in FIG. 21) refers to a line that passes through the axial center G of the guide unit 2, and orthogonally crosses the extending line (the y-axis in FIG. 21).

Further, the state in which the first flexible part 30k and the second flexible part 30h being indirectly in contact with each other means that the first flexible part 30k and the second flexible part 30h are continuously present via a wire or a tube (not shown) that is disposed between them.

With the characteristics described above, the bending and extending device 7 does not have a cross-section in which the centroid P of the flexible part 30 coincides with the axial center G in any portion in the longitudinal direction. Therefore, the bending and extending device 7 has an advantageous structure in terms of preventing unexpected local bending due to buckling.

Although the above explanation describes, according to FIG. 21, the flexible part 30k as the first flexible part and the flexible part 30h as the second flexible part, for easy understanding of the structure of the bending and extending device 7, this structure is merely an example. Among the flexible parts 30h, 30i, 30j, and 30k, a flexible part 30 in contact with the inner surface of the guide unit 2 corresponds to the second flexible part, and another flexible part 30 in contact with the second flexible part 30 either directly or indirectly corresponds to the first flexible part.

Furthermore, in the bending and extending device 7 shown in FIG. 18 and FIG. 19, as described above, the shape of the cross-section of the flexible parts 30h, 30i, 30j, and 30k corresponds to one of the fan-shaped planes obtained by equally dividing the internal cross-section of the guide unit 2. Further, with the state in which the combination of the cross-sections of the flexible parts 30h, 30i, 30j, and 30k substantially coincides with the circular shape of the internal cross-section of the guide unit 2, the gap S (FIG. 19) between the flexible parts 30h, 30i, 30j, and 30k, and the guide unit 2; and the distance D (FIG. 19) between two adjacent flexible parts 30 are reduced. Thus, even if a large external force is transmitted to the flexible parts 30h, 30i, 30j, and 30k through the guide unit 2, each flexible part 30 is prevented from buckling. This prevents the guide unit 2 from being largely bent halfway through the operation, or prevents generation of unexpected deformation in the guide unit 2, thereby maintaining the desired bending form.

Furthermore, in the state in which the flexible parts 30h, 30i, 30j, and 30k are positioned in the guide unit 2, since the side surface 33 of the first flexible part 30 becomes parallel to the side surface 33 of another flexible part 30 opposite thereto, the first flexible part 30 and the other flexible parts 30 are prevented from being twisted or crossed (for example, since the side surfaces 33h and 33j of the first flexible parts 33h and 33j become parallel, the flexible parts 33h and 33j are prevented from being twisted or crossed). Therefore, the sliding operation of the flexible parts 30h, 30i, 30j, and 30k may be smoothly performed, and the bending and extending device 6 can be bent into a desired shape.

Figure 22:
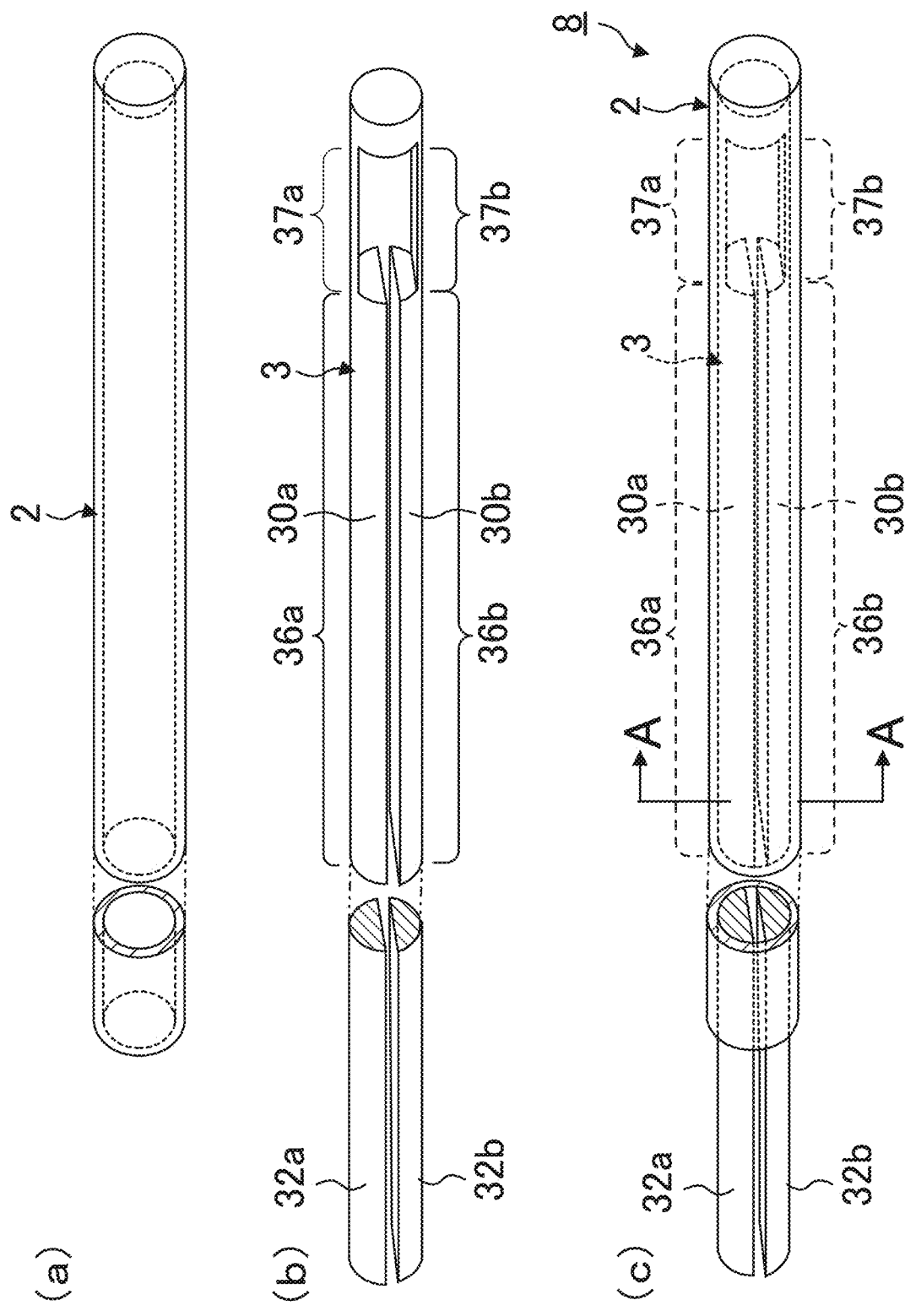
FIG. 22: (a) is a perspective view showing a guide unit, (b) is a perspective view showing a movable part, and (c) is a perspective view showing a bending and extending device according to a modification example of the present invention.
Figure 23:
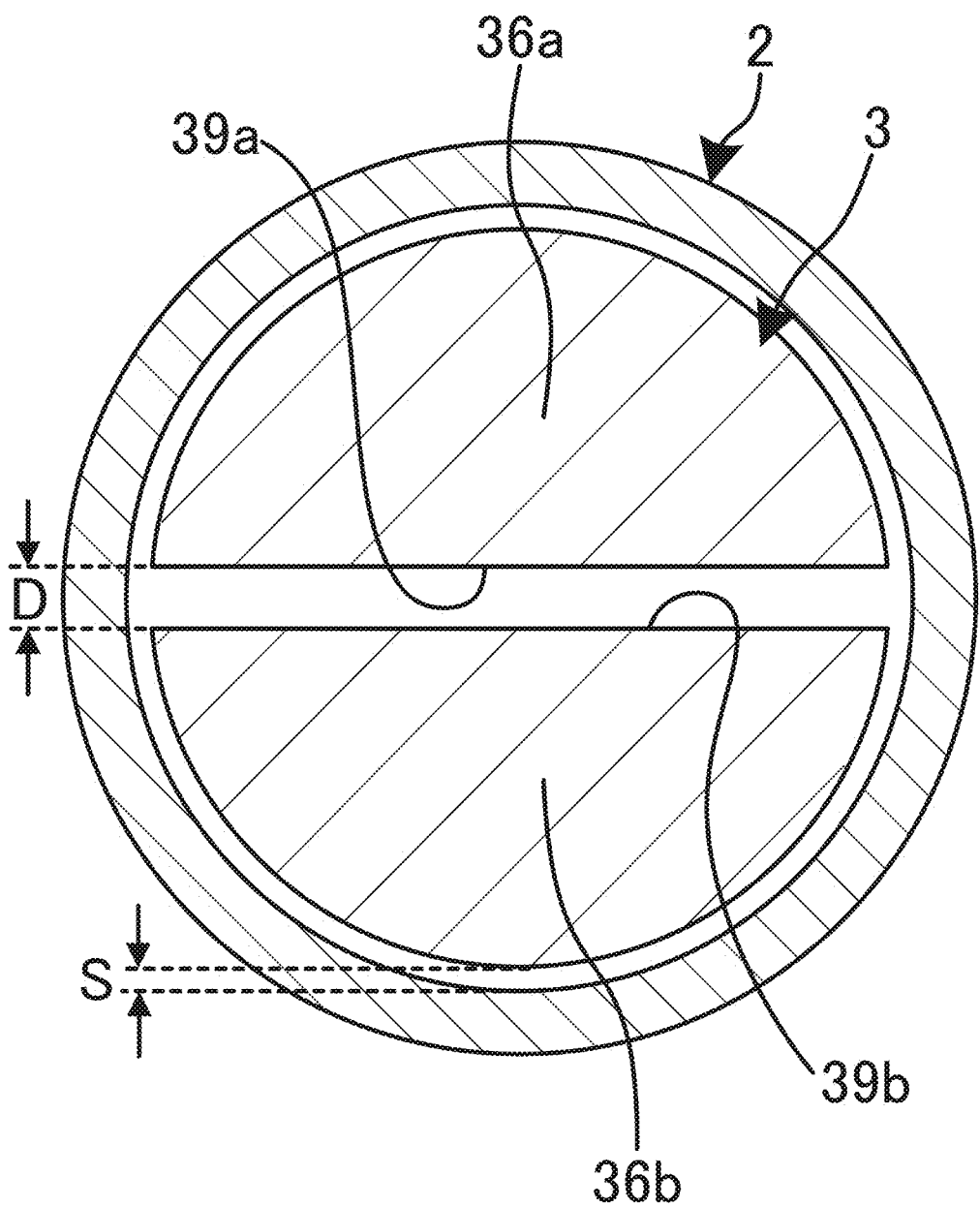
FIG. 23 is a cross-sectional view, taken along line A-A in FIG. 22 (c).

Further, in the bending and extending device 1 shown in FIGS. 1 to 10, the bending and extending device 5 shown in FIGS. 11 to 13, the bending and extending device 6 shown in FIGS. 14 to 17, and the bending and extending device 7 shown in FIGS. 18 to 21, the range (hereinafter referred to as a divided range) of the flexible part 30 whose cross-sectional shape corresponds to the plane obtained by equally dividing the internal cross-section of the guide unit 2 constitutes the entire flexible part 30; however, the bending and extending devices 1, 5, 6, and 7 may be deformed so that the divided range constitutes only a part of the flexible part 30. FIGS. 22 and 23 show an example in which the bending and extending device 1 shown in FIGS. 1 to 10 is modified as described above. The bending and extending device thus modified is specifically explained below, with reference to the example shown in FIGS. 22 and 23. FIG. 22 is a perspective view showing a bending and extending device 8 according to a modification example, and the guide unit and the movable part provided in the bending and extending device 8 (in FIG. 22, some portions of the bending and extending device are omitted). FIG. 23 is a cross-sectional view, taken along line A-A in FIG. 22 (c).

In the bending and extending device 8 shown in FIGS. 22 and 23, each of the flexible parts 30a and 30b has the divided range 36, and a range 37 thinner than the divided range 36 (hereinafter referred to as a thin range 37) (the flexible part 30a has a divided range 36a and a thin range 37a, and the flexible part 30b has a divided range 36a and a thin range 37b).

The cross-sectional shapes of the divided ranges 36a and 36b of the flexible parts 30a and 30b individually correspond to one of the semicircular planes obtained by equally dividing the internal cross-section of the guide unit 2 into two planes. The thin ranges 37a and 37b are positioned more closely to the distal end side of the flexible parts 30a and 30b than the divided ranges 36a and 36b.

Further, in a state in which the movable part 3 is inserted into the guide unit 2 and the divided ranges 36a and 36b of the flexible parts 30a and 30b are positioned in the guide unit 2, the shape of the combination of the cross-sections of the divided ranges 36a and 36b substantially coincides with the circular shape of the internal cross-section of the guide unit 2. Therefore, the gap S (FIG. 23) between the divided ranges 36a and 36b and the guide unit 2, and the distance D (FIG. 23) between the divided ranges 36a and 36b are reduced. Further, the side surface 39a of the divided range 36a and the side surface 39b of the divided range 36b opposite thereto both form a plane extending in the axial direction of the guide unit 2, and become parallel to each other. Further, the proximal ends 32a and 32b of the flexible parts 30a and 30b are extended to the outside of the guide unit 2.

In addition to the same effects as those of the bending and extending device described above, the bending and extending device 8 shown in FIGS. 22 and 23 may be designed to enable bending with a partially different curvature. The reasons therefor will be described below in detail.

Figure 24:
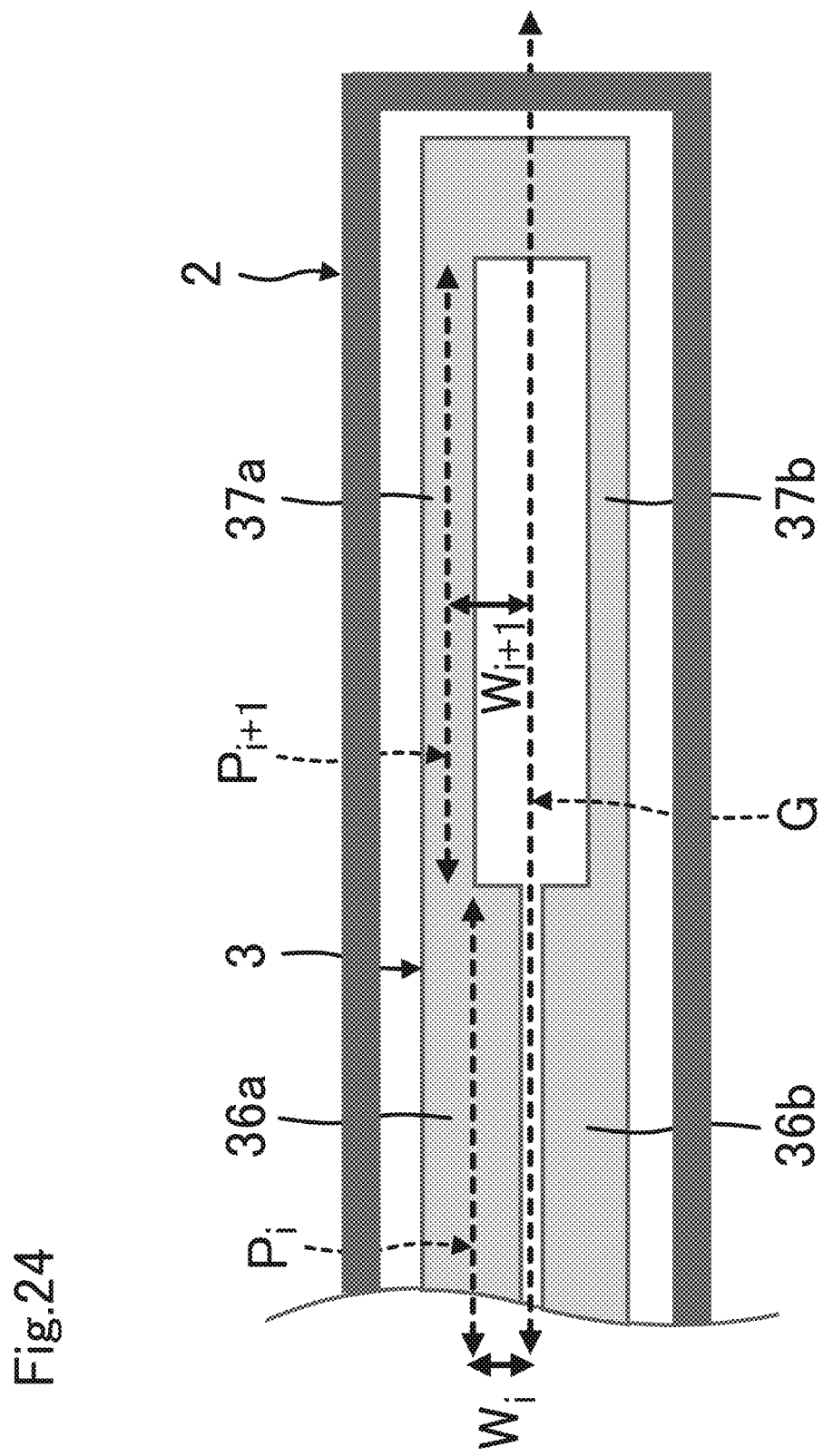
FIG. 24 is a schematic cross-sectional view showing the distal end side of a bending and extending device of a modification example.
Figure 25:
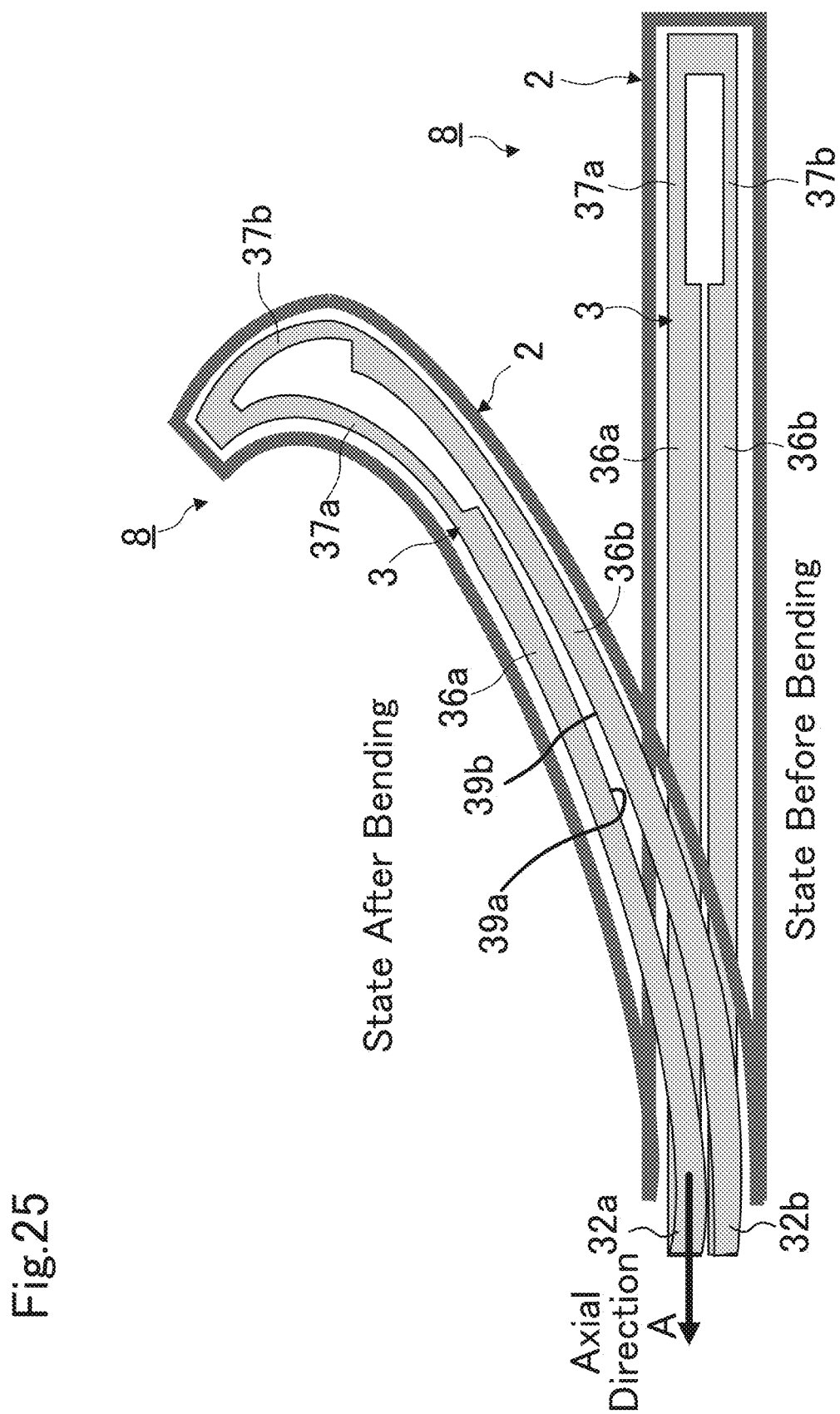
FIG. 25 is a schematic cross-sectional view showing a state before bending, and a state after bending, of a bending and extending device of a modification example.
Figure 26:
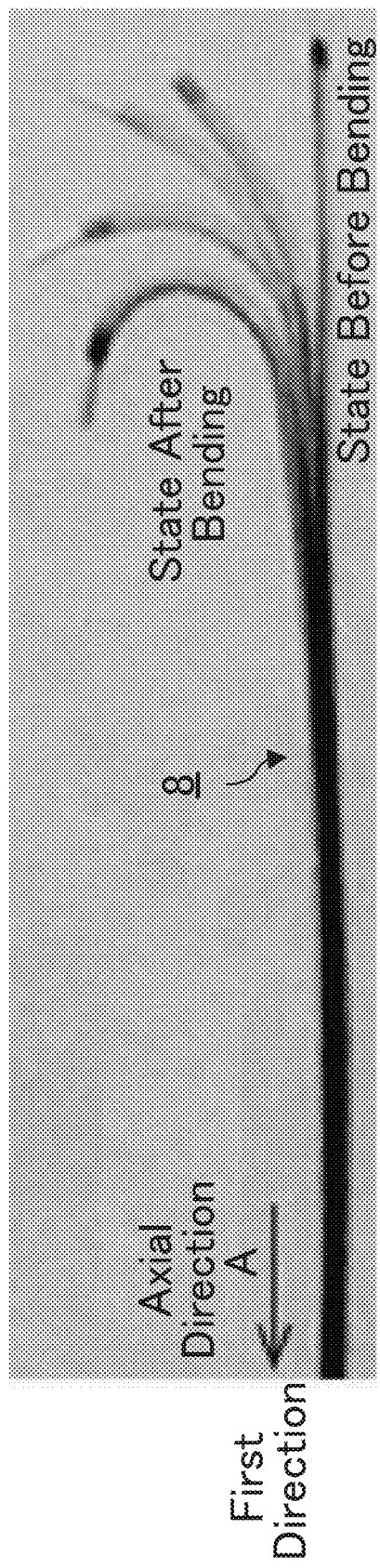
FIG. 26 is an image showing a state before bending, and a state after bending, of a bending and extending device of a modification example.

In the bending and extending device of the present invention described thus far, including the bending and extending device 8 as a modification example shown in FIGS. 22 and 23, the curvature $\Phi_{i+1}$ of the flexible part 30 at an arbitrary position (hereinafter referred to as position i+1) in the longitudinal direction thereof is equal to a value obtained by multiplying the curvature $\Phi_i$ of the flexible part 30 at the immediately preceding position (hereinafter referred to as position i) by a predetermined value A. The predetermined value A is determined according to the rigidity $K_{i+1}$ of the flexible part 30 at the position i+1, the distance $W_{i+1}$ between the axial center G of the guide unit 2 and the centroid $P_{i+1}$ of the flexible part 30 at the position i+1, the rigidity $K_i$ of the flexible part 30 at the position i, and the distance $W_i$ between the axial center G of the guide unit 2 and the centroid $P_i$ of the flexible part 30 at the position i. Further, under the condition in which the rigidity $K_{i+1}$ at the position i+1 and the rigidity $K_i$ at the position i are identical, by setting the distance $W_{i+1}$ at the position i+1 to be longer than the distance $W_i$ at the position i, the predetermined value A increases. As a result, the curvature ϕi+1 at the position i+1 becomes greater than the curvature ϕi at the position i. Based on this, the bending and extending device 8 shown in FIGS. 22 and 23 is structured such that the thin ranges 37a and 37b at the distal end side are thin, and the divided ranges 36a and 36b are thick; and, as shown in FIG. 24, the distance $W_{i+1}$ between the axial center G and the centroid $P_{i+1}$ in the thin range 37 at the distal end side is greater than the distance $W_i$ between the axial center G and the centroid $P_i$ in divided range 36. With this structure, when the proximal end 32 of the flexible part 30 is slid, as shown in FIGS. 25 and 26, bending with a large curvature is generated in the distal end side having the thin ranges 37a and 37b, and bending with a small curvature is generated in the proximal end side having the divided ranges 36a and 36b; thus, the bending and extending device 8 has a bending design with a curvature that partially varies. In contrast to the above, it is also possible to generate bending with a small curvature at the distal end side, and generate bending with a large curvature at the proximal end side, by forming the thin ranges 37a and 37b to be closer to the proximal end side than the divided ranges 36a and 36b.

Further, in the bending and extending device of the present invention, the number of the flexible parts 30 constituting the movable part 3 is not limited to 2 to 4, as in the examples shown in FIGS. 1 to 26; and any plural number other than 2 to 4 of the flexible parts 30 may be used. When three or more flexible parts 30 are used, the bending can be caused in any vertical and horizontal direction from the axial center without rotating the flexible parts 30 and the guide unit 2 about the axis, as in the bending and extending devices 6 and 7 shown in FIGS. 14 to 21 (when the number of the flexible parts 30 is represented by n, it is possible to bend the bending and extending device in 2n directions).

Further, when the number of the flexible parts 30 is a plural number other than 2 or 4, for example, the cross-section of the divided range 36 of each flexible part 30 corresponds to one of the planes obtained by equally dividing the internal cross-section of the guide unit 2 by the number of the flexible parts 30. Further, in a state in which the movable part 3 is inserted into the guide unit 2 so that the divided range 36 of the flexible part 30 is positioned in the guide unit 2, the shape of the combination of the cross-sections of the divided ranges 36 of each flexible part 30 substantially coincides with the shape of the internal cross-section of the guide unit 2, and the side surface of the first flexible part 30 and the side surface of another flexible part 30 opposite thereto become parallel to each other. With this structure, the gap between the flexible part 30 and the guide unit 2, and the distance between the plural flexible parts 30 can be sufficiently reduced. Therefore, even when a large external force is applied to the guide unit 2, it is possible to maintain a desired bending form.

Further, in the bending and extending device of the present invention, the shape of the cross-section of the flexible part 30 may not correspond to the shape obtained by equally dividing the internal cross-section of the guide unit 2. In this case as well, as described above, by structuring the bending and extending device so that a cross-section in which the centroid P of the flexible part 30 coincides with the axial center G is not present in any portion in the longitudinal direction, the bending and extending device of the present invention has an advantageous structure in terms of preventing unexpected local bending due to buckling.

Figure 27:
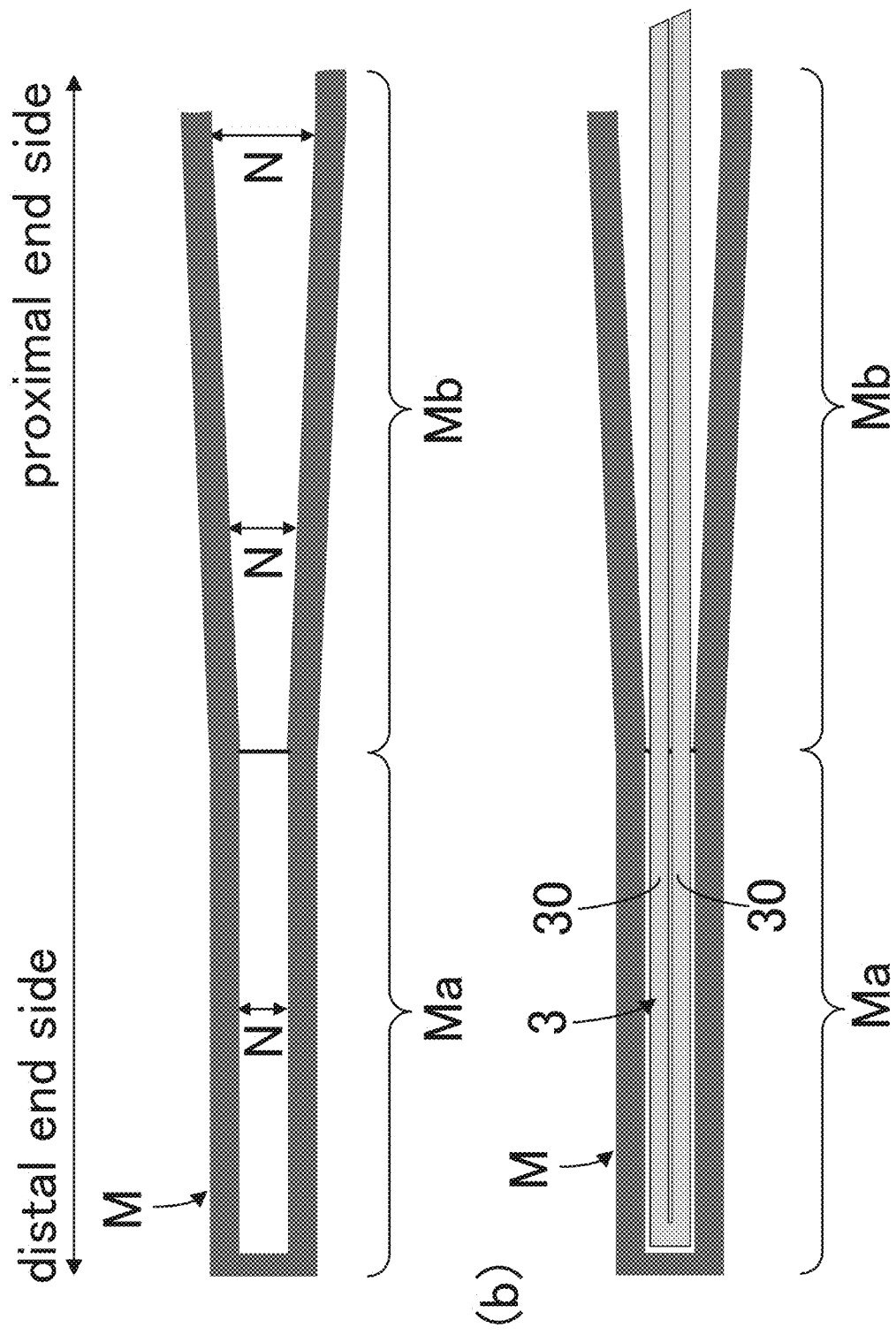
FIG. 27 is a cross-sectional view showing a tubular body constituting the outline of a movable catheter.
Figure 28:
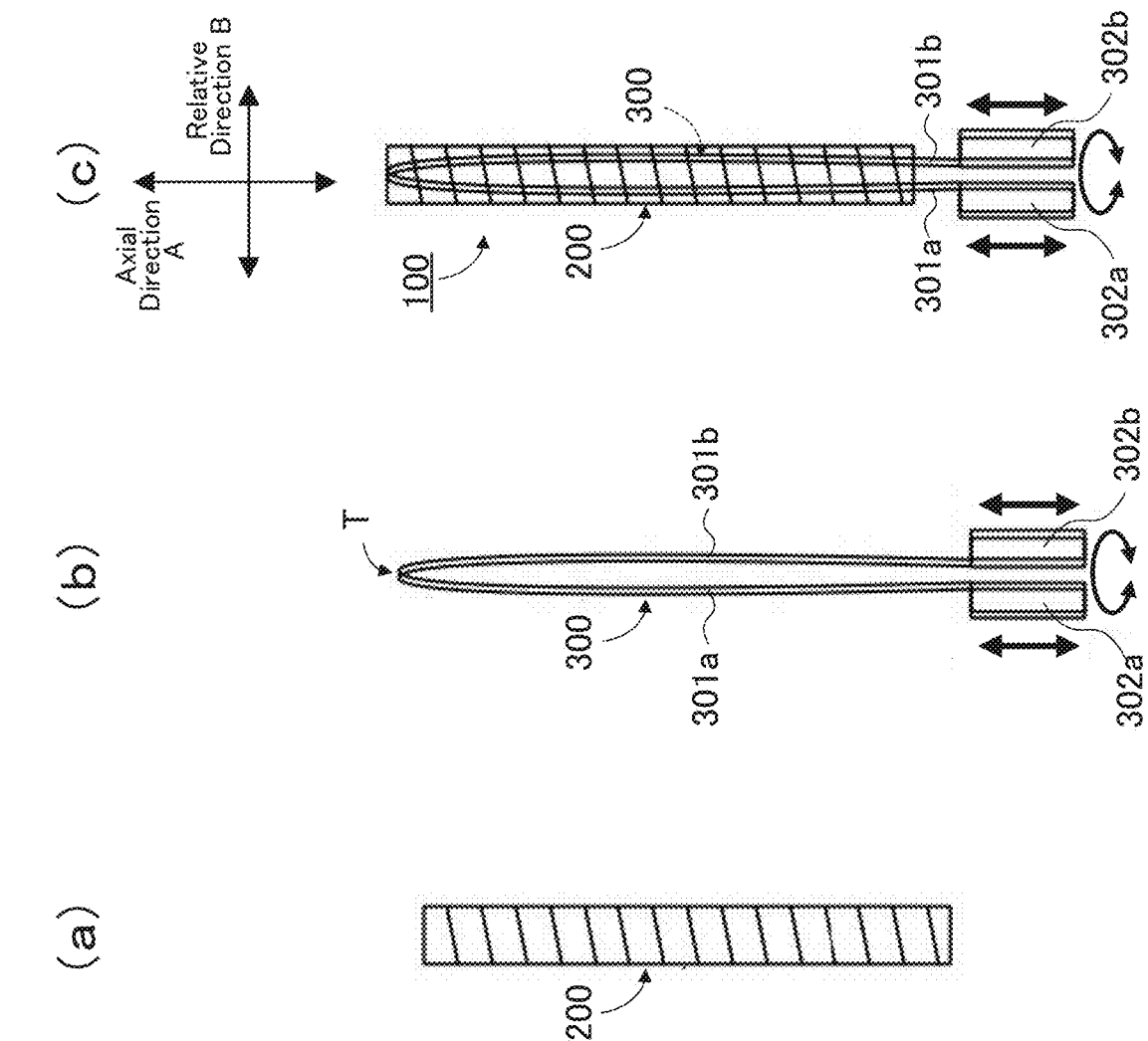
FIG. 28 is a figure showing a previously known bending and extending device. (a) is a lateral view showing a guide unit, (b) is a lateral view showing a movable part, and (c) is a lateral view showing a previously known bending and extending device.
Figure 29:
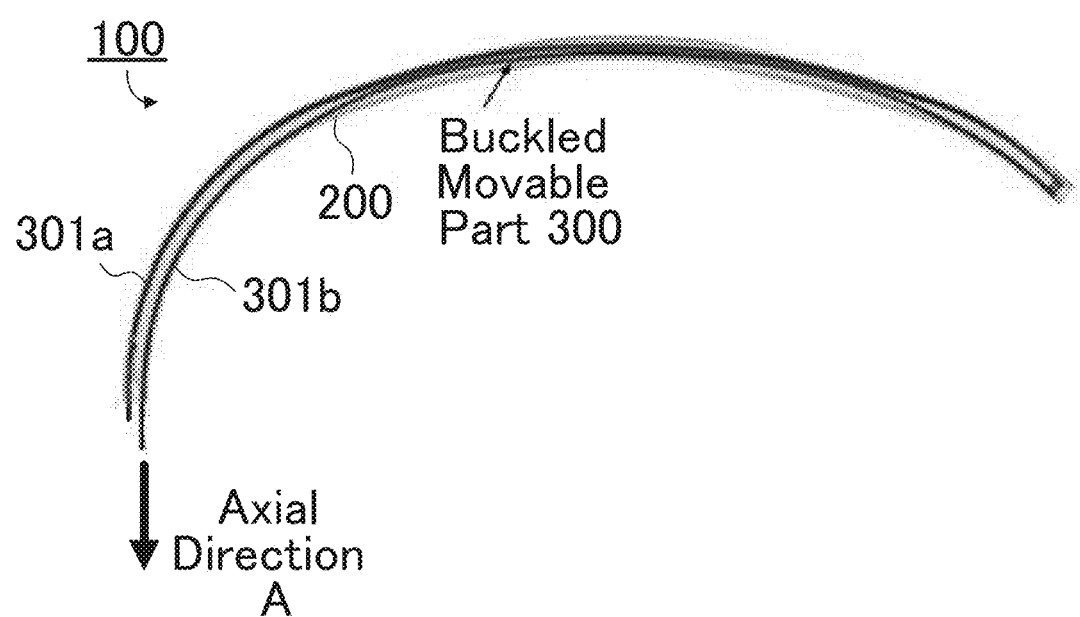
FIG. 29 is a schematic lateral view showing a state in which a movable part is buckled.
Figure 30:
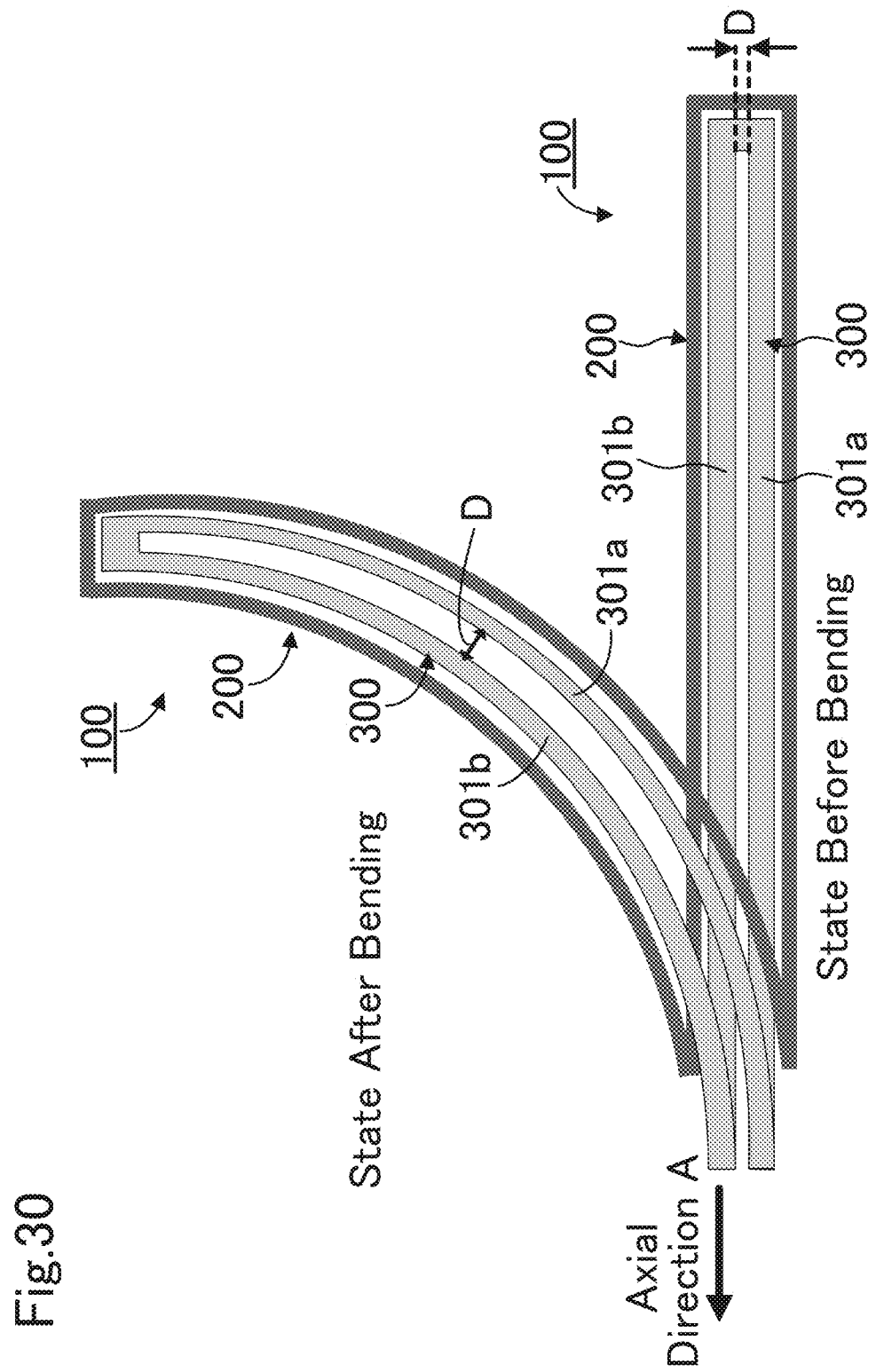
FIG. 30 is a schematic cross-sectional view showing a state before bending, and a state after bending, of a previously known bending and extending device.

Further, in recent years, a tubular body, such as the tubular body M shown in FIG. 27 (*a*), for constituting the outline of a movable catheter has been used. The tubular body M is structured so that the inner diameter N of the range Ma in the distal end side is constant, and the inner diameter N of the range Mb in the proximal end side gradually increases as it approaches the proximal end. When the movable part 3 is movably inserted into the tubular body M as shown in FIG. 27 (*a*) so as to bend the tubular body M, the range Ma in the distal end side of the tubular body M having a constant inner diameter N corresponds to the guide unit. With a structure in which a cross-section in which the centroid of the flexible part 30 coincides with the axial center of the range Ma (guide unit) is not present in the range Ma (guide unit), it is possible to prevent unexpected local bending due to buckling.

REFERENCE NUMERALS 1, 5, 6, 7, 8: Bending and extending device
2: Guide unit
3: Movable part
30, 30*a*, 30*b*, 30*c*, 30*d*, 30*e*, 30*f*, 30*g*, 30*h*, 30*i*, 30*j*, 30*k*: Flexible part
32, 32*a*, 32*b*, 32*c*, 32*d*, 32*e*, 32*f*, 32*h*, 32*j*: Proximal end
33, 33*a*, 33*b*, 33*c*, 33*d*, 33*e*, 33*f*, 33*h*, 33*j*: Side surface
36, 36*a*, 36*b*: Divided range
37, 37*a*, 37*b*: Thin range
G: Axial center
T: Contact point
Y: Extending line
X: Predetermined straight line

The invention claimed is:

1. A bending and extending device, comprising:
an elastic hollow guide unit; and
a movable part to be movably inserted into the guide unit, wherein:
the guide unit has a uniform cross-sectional shape and a uniform cross-sectional size along an entire length of the guide unit in which the movable part is inserted into the guide unit;
the movable part comprises a plurality of belt-like flexible parts and a distal end portion extending in a direction perpendicular to the flexible parts;
each flexible part has a divided range and a thin range that is thinner than the divided range, the thin ranges are positioned more closely to a distal end side of the flexible parts than the divided ranges;
the distal end portion connects the thin ranges of the flexible parts at distal ends of the flexible parts;
a combination of cross-sections of the divided ranges of the flexible parts has a same geometric shape as an internal cross-section of the guide unit;
the movable part causes the plurality of flexible parts to be bent in a direction perpendicular to an axial direction of the guide unit by sliding one of proximal ends of the plurality of flexible parts in the axial direction of the guide unit (hereinafter referred to as a flexible part sliding operation);
the distal ends of the flexible parts are inside the guide unit during the flexible part sliding operation;
when, by the flexible part sliding operation, a cross-section in which a contact point of a second flexible part of the flexible parts and an inner surface of the guide unit is present on an extending line extending from a line segment connecting the centroid of a first flexible part of the flexible parts and the axial center of the guide unit and in which the first flexible part and the second flexible part are directly or indirectly in contact with each other is generated, and when the cross-section is divided into two ranges by a predetermined straight line, the centroid of the first flexible part is not positioned in a range in which the contact point of the second flexible part and the inner surface of the guide unit is present; and
the predetermined straight line is a line that passes through the axial center of the guide unit, and that orthogonally crosses the extending line,
wherein, when the flexible parts are in a non-bent position, a thin range gap exists between the thin ranges and extends in the direction perpendicular to the axial direction, a divided range gap exists between the divided ranges and extends in the direction perpendicular to the axial direction, and the thin range gap is larger than the divided range gap in the direction perpendicular to the axial direction.

2. The bending and extending device according to claim 1, wherein the movable part has three or more flexible parts.

3. The bending and extending device according to claim 1, wherein the internal cross-section of the guide unit has a circular shape; the movable part has two flexible parts; and the cross-sectional shape of the divided range of each flexible part corresponds to one of semicircular planes obtained by equally dividing the internal cross-section of the guide unit into two planes.

4. The bending and extending device according to claim 1, wherein the internal cross-section of the guide unit has a rectangular shape; the movable part has two flexible parts; and the cross-sectional shape of the divided range of each flexible part corresponds to one of rectangular planes obtained by equally dividing the internal cross-section of the guide unit into two planes.

5. The bending and extending device according to claim 1, wherein the internal cross-section of the guide unit has a circular shape; the movable part has four flexible parts; and the cross-sectional shape of the divided range of each flexible part corresponds to one of fan-shaped planes obtained by equally dividing the internal cross-section of the guide unit into four planes.

6. The bending and extending device according to claim 1, wherein the plurality of flexible parts have elasticity greater than that of the guide unit.

7. The bending and extending device according to claim 6, wherein the guide unit is formed of a hyperelastic alloy such as β titanium, nickel titanium (nitinol), or stainless steel, a resin material, or rubber; and the plurality of flexible parts are formed to have a rigidity equal to or greater than that of the guide unit using β titanium, nickel titanium, polypropylene, an acrylic material, or PEEK (polyether ether ketone) resin.

8. The bending and extending device according to claim 1, wherein the movable part is rotatable in the circumferential direction of the guide unit.

9. The bending and extending device according to claim 1, wherein the guide unit has a closed distal end and an opened proximal end, and the movable part is movably inserted into the guide unit from the proximal end of the guide unit.

10. A method for bending and extending a bending and extending device, the bending and extending device comprising:

an elastic hollow guide unit; and a movable part to be movably inserted into the guide unit, wherein:

the guide unit has a uniform cross-sectional shape and a uniform cross-sectional size along an entire length of the guide unit in which the movable part is inserted into the guide unit;

the movable part is constituted, either partially or entirely, of a plurality of belt-like flexible parts, which extend in an axial direction of the guide unit and are connected at distal ends;

the movable part causes the plurality of flexible parts to be bent in a direction perpendicular to the axial direction of the guide unit by sliding one of proximal ends of the plurality of flexible parts in the axial direction of the guide unit (hereinafter referred to as a flexible part sliding operation);

the distal ends of the flexible parts are inside the guide unit during the flexible part sliding operation;

when, by the flexible part sliding operation, a cross-section in which a contact point of a second flexible part of the flexible parts and an inner surface of the guide unit is present on an extending line extending from a line segment connecting the centroid of a first flexible part of the flexible parts and the axial center of the guide unit and in which the first flexible part and the second flexible part are directly or indirectly in contact with each other is generated, and when the cross-section is divided into two ranges by a predetermined straight line, the centroid of the first flexible part is not positioned in a range in which the contact point of the second flexible part and the inner surface of the guide unit is present; and the predetermined straight line is a line that passes through the axial center of the guide unit, and that orthogonally crosses the extending line;

the method comprising:

an insertion step of inserting the movable part into the guide unit so that the movable part extends in the axial direction of the guide unit;

a sliding step of sliding a proximal end of the first flexible part, which is one of the plurality of flexible parts, relative to a proximal end of another flexible part in the axial direction of the guide unit;

an inverse sliding step of sliding the proximal end of the first flexible part in the direction opposite to the direction upon the bending;

wherein:

by the sliding step, bending is generated in the movable part at the distal ends of all of the flexible parts serving as a node in a direction perpendicular to the axial direction of the guide unit, and the movable part thus bent comes into contact with a part or the entirety of the inner surface of the guide unit, thereby causing the guide unit to be bent in the perpendicular direction;

the distal ends of the flexible parts are inside the guide unit during the sliding step; and by the inverse sliding step, the movable part thus bent is extended and comes into contact with a part or the entirety of the inner surface of the guide unit, thereby extending the guide unit.

11. The bending and extending method according to claim 10, further comprising a rotation step of rotating the movable part inserted in the guide unit in the circumferential direction of the guide unit, thereby changing the direction of the movable part, wherein the change in the direction of the movable part by the rotation step changes the direction of the bending generated in the guide unit in the sliding step.

\* \* \* \* \*